US009968562B2

(12) United States Patent
Lescure et al.

(10) Patent No.: US 9,968,562 B2
(45) Date of Patent: May 15, 2018

(54) FORMULATIONS FOR ORAL DELIVERY OF ADSORBENTS IN THE GUT

(75) Inventors: Francois Lescure, Pechbusque (FR); Jean De Gunzburg, London (GB)

(73) Assignee: DA VOLTERRA, Paris (FR)

( * ) Notice: Subject to any disclaimer, the term of this patent is extended or adjusted under 35 U.S.C. 154(b) by 0 days. days.

(21) Appl. No.: 13/580,144

(22) PCT Filed: Feb. 23, 2011

(86) PCT No.: PCT/EP2011/052682
§ 371 (c)(1),
(2), (4) Date: Oct. 31, 2012

(87) PCT Pub. No.: WO2011/104275
PCT Pub. Date: Sep. 1, 2011

(65) Prior Publication Data
US 2013/0052269 A1 Feb. 28, 2013

(30) Foreign Application Priority Data
Feb. 23, 2010 (EP) .................................... 10305179

(51) Int. Cl.
A61K 9/14 (2006.01)
A61K 9/50 (2006.01)
A61K 9/16 (2006.01)
A61K 31/00 (2006.01)
A61K 31/731 (2006.01)
A61K 33/44 (2006.01)

(52) U.S. Cl.
CPC .......... A61K 9/5073 (2013.01); A61K 9/1652 (2013.01); A61K 9/5015 (2013.01); A61K 9/5026 (2013.01); A61K 9/5042 (2013.01); A61K 9/5047 (2013.01); A61K 31/00 (2013.01); A61K 31/731 (2013.01); A61K 33/44 (2013.01)

(58) Field of Classification Search
None
See application file for complete search history.

(56) References Cited

U.S. PATENT DOCUMENTS

| 3,917,821 | A | | 11/1975 | Manes | |
|---|---|---|---|---|---|
| 4,761,284 | A | * | 8/1988 | Nishimura | 424/125 |
| 5,364,636 | A | | 11/1994 | Ochi | |
| 5,380,526 | A | * | 1/1995 | Ise | 424/125 |
| 5,597,564 | A | * | 1/1997 | Ying | 424/94.65 |
| 5,900,252 | A | * | 5/1999 | Calanchi et al. | 424/459 |
| 6,153,170 | A | | 11/2000 | Camilleri et al. | |
| 6,277,179 | B1 | | 8/2001 | Reymonet | |
| 8,075,883 | B2 | | 12/2011 | Shibata et al. | |
| 8,388,984 | B2 | * | 3/2013 | Huguet et al. | 424/400 |
| 2002/0155165 | A1 | * | 10/2002 | Nakanishi | 424/600 |
| 2004/0141963 | A1 | * | 7/2004 | Umekawa et al. | 424/125 |
| 2005/0013788 | A1 | * | 1/2005 | Held et al. | 424/70.16 |
| 2006/0083690 | A1 | | 4/2006 | Chang | |
| 2006/0210631 | A1 | | 9/2006 | Patel et al. | |
| 2006/0222714 | A1 | * | 10/2006 | Aoyagi | A61K 9/1652 424/489 |
| 2007/0141046 | A1 | * | 6/2007 | Von Blucher et al. | 424/125 |
| 2007/0196437 | A1 | * | 8/2007 | Hamaker et al. | 424/439 |
| 2007/0243268 | A1 | * | 10/2007 | Jaffe | 424/702 |
| 2008/0031867 | A1 | * | 2/2008 | Huguet et al. | 424/94.6 |
| 2008/0044477 | A1 | * | 2/2008 | Sonobe et al. | 424/489 |
| 2008/0089943 | A1 | * | 4/2008 | Frapaise | 424/489 |
| 2008/0107589 | A1 | * | 5/2008 | von Blucher et al. | 423/449.1 |
| 2009/0148538 | A1 | * | 6/2009 | Fischer et al. | 424/600 |
| 2010/0036002 | A1 | * | 2/2010 | Ishibashi | A61K 9/2013 514/781 |
| 2011/0021641 | A1 | | 1/2011 | Behrend et al. | |

FOREIGN PATENT DOCUMENTS

| EP | 0967176 A1 | 12/1999 |
|---|---|---|
| EP | 1525886 A1 | 4/2005 |
| KR | 10-2010-0001892 A | 1/2010 |
| WO | 8801506 A1 | 3/1988 |
| WO | 0181249 A1 | 11/2001 |
| WO | 2005021057 A1 | 3/2005 |
| WO | 2006122835 A1 | 11/2006 |
| WO | 2007132022 A2 | 11/2007 |

(Continued)

OTHER PUBLICATIONS

Khan et al., A pH-dependent colon targeted oral drug delivery system using methacrylic acid copolymers, I. manipulation of drug release using Eudragit L100-55 and Eudragit S100 combinations, J. Contrl. Release, 1999, vol. 58, pp. 215-222.*
Chourasia et al., Pharmaceutical approaches to colon targeted drug delivery systems, J. Pharmacy Pharmaceutical Sci., 2003, vol. 6, pp. 33-66.*
Kleinebudde et al. (Use of k-carrageenan as alternative pellitisation aid to microcrystalline cellulose in extrusion/spheronisation. I. Influenece of type and fraction of filler, Eur. J. Pharm. and Biopharm., 2006, vol. 63, pp. 59-67).*
Cabot, activated carbon, 2015, pp. 1-13.*
Horkay et al. Osmotic swelling of polyacrylate hydrogel in physiological salt solution, Biomacromolecules, 2000, vil. 1, p. 84.*
Remon et al. (In vitro evaluation of coating polymers for enteric coating and human ileal targeting, Int. J. Pharm., 2005, vol. 298, p. 26-37).*
Sirisha et al., A review of pellets and palletization process—a multiparticulate drug delivery system, IJPSR, 2013, vol. 4, p. 2145-2158 (Year: 2013).*

(Continued)

Primary Examiner — Bethany P Barham
Assistant Examiner — Ping Cao
(74) Attorney, Agent, or Firm — Arrigo, Lee, Guttmann & Mouta-Bellum LLP

(57) ABSTRACT

The invention relates to a formulation for the delayed and controlled delivery of an adsorbent into the lower intestine of mammals. The formulation includes a carrageenan and an adsorbent, such as activated charcoal. The invention further relates to uses of this formulation, in particular to pharmaceutical uses. In one embodiment, the formulation is used to eliminate or reduce the side effects in the intestine, in particular in the colon, of pharmaceutical agents that are administered as a treatment for a disorder, but that have side effects when they reach the late ileum, the caecum or the colon.

19 Claims, 14 Drawing Sheets

(56) References Cited

FOREIGN PATENT DOCUMENTS

| WO | WO2008059062 | * | 5/2008 | ............. A61K 38/00 |
|---|---|---|---|---|
| WO | WO2008084676 | * | 7/2008 | ............. A61K 47/38 |
| WO | 2011036400 A1 | | 3/2011 | |

OTHER PUBLICATIONS

Manivannan et al., Multiparticulate drug delivery systems: pellet and palletization technique, Drug Invention Today, 2010, vol. 2, p. 233 (Year: 2010).*

Gardiner, K., et al., "Adsorbents as antiendotoxin agents in experimental colitis", "Gut", Jan. 1993, pp. 51-55, vol. 34.

Arias, J., et al., "Two methods of large-scale extraction of an antibiotic produced by Myxococcus coralloides", "Microbios", 1979, pp. 19-23 (Abstract), vol. 25, No. 99.

Arias, J., et al., "Two methods of large-scale extraction of an antibiotic produced by Myxococcus coralloides", "Microbios.", 1979, pp. 19-23 (Abstract), vol. 25, No. 99.

Denti, E., et al., "Adsorption Characteristics of Cellulose Acetate Coated Charcoals", "J. Biomed. Mater. Res.", 1975, pp. 143-150, vol. 9.

Khalil, S., et al., "The In Vitro Adsorption of Some Antibiotics on Antacids", "Pharmazie", 1976, pp. 105-109, vol. 31, No. 2.

Khoder, M., et al., "Removal of ciprofloxacin in simulated digestive media by activated charcoal entrapped within zinc-pectinate beads", "International Journal of Pharmaceutics", May 23, 2009, pp. 251-259, vol. 379.

Khoder, M., et al., "Removal of residual colonic ciprofloxacin in the rat by activated charcoal entrapped within zinc-pectinate beads", "European Journal of Pharmaceutical Sciences", Jul. 3, 2010, pp. 281-288, vol. 41, No. 2.

Kramer Consumer Healthcare, "Charcoal Plus DS", http://www.charcoalplus.com (as accessed on May 10, 2011), p. 1.

Manes, M., et al., "Easily Swallowed Formulations of Antidote Charcoals", "Clinical Toxicology", 1974, pp. 355-364, vol. 7, No. 4.

Manes, Milton, and Mann, Jack P.; "Easily Swallowed Formulations of Antidote Charcoals", Clinical Toxicology, 7(4) (1974), http://dx.doi.org/10.3109/15563657408987998, pp. 355-364.

* cited by examiner

FORMULATIONS FOR ORAL DELIVERY OF ADSORBENTS IN THE GUT

CROSS-REFERENCE TO RELATED APPLICATIONS

This application is a U.S. national phase under the provisions of 35 U.S.C. § 371 of International Patent Application No. PCT/EP2011/052682 filed Feb. 23, 2011, which in turn claims priority of European Patent Application No. 10305179.3 filed Feb. 23, 2010. The disclosures of such international patent application and European priority patent application are hereby incorporated herein by reference in their respective entireties, for all purposes.

The invention relates to a formulation for the delayed and controlled delivery of an adsorbent into the lower intestine of mammals. The invention further relates to uses of this formulation, in particular to pharmaceutical uses.

BACKGROUND OF THE INVENTION

When antibiotics are administered, either orally or parenterally, a significant fraction of the administered dose reaches the late ileum or colon in an active form and comes into close contact with the bacterial population that is present in the colon. The alarming consequences of this have been known for years and constitute the subject of a ECDC/EMEA Joint Technical Report called "The bacterial challenge: time to react, A call to narrow the gap between multidrug-resistant bacteria in the EU and the development of new antibacterial agents" published in September 2009. The residual antibiotic exerts a selective pressure on the bacteria present in the colon and provokes the emergence and development of bacteria resistant to the antibiotic. Because the genetic determinants of resistance to various antibiotics are often physically linked on mobile genetic elements such as plasmids and transposons, the treatment with a single antibiotic often selects for the simultaneous presence of several antibiotic resistance genes, thus explaining how multi-antibiotic resistance can emerge very fast.

As a result of this process, the patient or the animal that has received an antibiotic treatment becomes very rapidly and strongly colonized by antibiotic-resistant bacteria. This can result in complicated further infections by resistant bacteria as well as the dissemination of resistance to other bacteria, and ultimately the environment.

It is now widely accepted that the selection and dissemination of such resistant bacteria is a major factor that increases significantly the dissemination of bacterial resistance to antibiotics both in the community and in hospitals. Levels of bacterial resistance are currently extremely high and increasing year after year becoming a major public health problem worldwide that could lead to major outbreaks of infections very difficult to treat with available antibiotics either in humans or in animals.

Besides producing antibiotic-resistant bacteria, antibiotics that reach the colon in active form will also profoundly alter the composition of the commensal flora and eliminate susceptible bacterial species. Among those bacteria, susceptible anaerobic bacteria can be eliminated; they are known to play a major physiological role in the intestine of normal subjects and animals. For example, they act to prevent colonization by exogenous potentially pathogenic microorganisms such as *Clostridium difficile* and/or *Candida* sp, and/or multiresistant exogenous bacteria such as Vancomycin-resistant enterococci. It is therefore essential to prevent elimination of such useful bacteria to prevent adverse effects of antibiotics, which can lead to the appearance of pathologic signs and symptoms, such as post-antibiotic diarrhea or the more severe forms of pseudomembranous colitis, *Candida* genital infections, particularly in women, or antibiotic-resistant systemic infections in hospitalized patients, particularly those in intensive care.

One way to prevent such adverse effects of antibiotic treatments is to eliminate residual antibiotics that arrive in the caecum and colon; in the recent years, there have been two different approaches to achieve this goal. One has been the delivery to the gut of enzymes that specifically degrade antibiotics (such as those described in US20050249716). Alternatively, the formulation of an adsorbent for a site-specific intestinal delivery has been proposed in applications WO2006/122835 and WO2007/132022. The adsorbent would act by sequestering the antibiotic before it can affect susceptible bacteria in the caecum and colon. This approach would enable to broaden the spectra of antibiotics that may be eliminated as compared to previous approaches based on antibiotic-specific enzymes. Adsorbents, and in particular activated charcoal, are very challenging products to formulate because of their physicochemical properties such as low density, hydrophobicity, wetting properties, etc. Attempting to formulate activated charcoal for an intestinal site-specific delivery of an oral dose is not possible using conventional direct compression because of the very low cohesive properties of activated charcoal. Even simple wet granulation and compression lead to tablets exhibiting poor adsorption properties and poor disintegration profile. Enzyme-based delivery systems have been proposed to overcome these problems. These systems are based on their degradation and subsequent release of their content in the colon as a result of the action of colonic enzymes on a polymer encapsulating the adsorbent. A representative system implements pectin beads specifically degraded by pectinolytic enzymes which are produced in the colon of many mammals by bacteria of the commensal flora (such as those described in WO2006/122835). However, this system presents limitations such as low adsorbent content and difficulties in up scaling the production of pectin beads. Also, variability in the amount of pectinolytic enzymes present in the colon has led to variability in the delivery of the adsorbent. Solid dosage forms, either in single dosage form such as tablet or in a multi-dispersed pellet formulation, have also been proposed, with an excellent yield and adsorbent content (WO2007/132022). However, even though formulations could be made in a straightforward manner, their disintegration properties and the adsorption efficiency of the released adsorbent could be improved in a more satisfactory manner.

It would be advantageous to develop a formulation appropriate for the delayed release of an adsorbent in the later parts of the gastrointestinal tract yet preserving as much as possible the adsorption characteristics of the adsorbent. It would also be advantageous to produce a formulation with an improved adsorbent-release profile, with a release of the adsorbent at a place and time in the gastrointestinal tract where no more antibiotic is absorbed. This would prevent any interaction of the adsorbent with the normal absorption process of antibiotics, or any other pharmaceutical product, when given simultaneously by oral route.

Such formulation would be advantageous in removing residual antibiotics and/or their active metabolites from the intestinal tract while being able to be co-administered with large number of antibiotics and to reduce unwanted antibiotic-associated side-effects such as diarrhea, abdominal pain, and bacterial resistance to antibiotics. It would also be advantageous to have formulations that provide a specific release of an adsorbent in the lower part of the gastrointestinal tract, specifically in the late ileum, the caecum, or the colon.

Such formulation would also be advantageous in reducing or eliminating the side effects of pharmaceutical agents or metabolites thereof in the late ileum, caecum and colon. Such pharmaceutical agents are for example agents which are administered to treat a disease state, but which have side effects when they reach the lower part of the gastroinstestinal tract, specifically in the late ileum, the caecum, or the colon. Representative, non limiting, examples of such pharmaceutical agents include irinotecan and its metabolite SN-38, diacerhein, Pancrelipase (such as Pancrease, Creon, Zenpep), Phosphodiesterase 4 inhibitors used in the treatment of chronic obstructive pulmonary disease such as Roflumilast or Cilomilast, or anti-mitotic and anti-inflammatory drugs such as colchicine.

Furthermore, such formulation would be advantageous in the treatment of disease states characterized by the accumulation of substances in the lower part of the gastroinstestinal tract, this accumulation being responsible for the development of a number of pathological conditions. For example, the formulation can be useful for the treatment of conditions such as, but not limited to, hepatic encephalopathy, irritable bowel syndrome, chronic renal disease, *C. difficile* associated diarrhea or antibiotic associated diarrhea. Representative substances which can be adsorbed by the formulation disclosed herein include, but are not limited to, ammonia, indoles, advanced glycation end products (AGEs) and certain bacterial toxins.

More generally, the formulation of the invention can be used in the treatment of a condition, either pathological or not, which is caused, maintained and/or enhanced by the presence, or the presence in excess quantities, of certain substances in the lower part of the gastrointestinal tract, specifically in the late ileum, the caecum, or the colon.

The present invention provides such formulations and methods of preparation and use thereof.

SUMMARY OF THE INVENTION

Formulations useful for delivering an adsorbent to the late ileum, the caecum or the colon are provided. In one embodiment, a composition comprising a mixture of an adsorbent with carrageenan, preferably in the form of a pellet, is provided. In one aspect of this embodiment, the adsorbent is activated charcoal, and in another aspect of this embodiment, the carrageenan is a kappa-carrageenan. The amount of carrageenan is typically in the range of between 5% and 25%, more preferably between 10% and 20%, by weight of the mixture.

The composition comprising the mixture can be used to form a core. In one embodiment, the core is provided with a layer of a coating such that the adsorbent is released from the formulation in the lower part of the intestine, i.e in the late ileum, caecum and/or colon. Representative coatings allowing release at the desired part of the intestine include pH-dependent enterosoluble polymers, materials that are specifically degraded in the colonic environment by the action of microorganisms and/or the reductive environment found there (e.g. azopolymers and disulphide polymers, polysaccharides, in particular amylose or pectin (e.g. pectin crosslinked with divalent cations such as calcium pectinate or zinc pectinate), chondroitin sulphate and guar gum). Representative pH-dependent enterosoluble polymers include cellulose acetate trimellitate (CAT), cellulose acetate phthalate (CAP), anionic copolymers based on methylacrylate, methylmethacrylate and methacrylic acid, hydroxypropyl methylcellulose phthalate (HPMCP), hydroxypropylmethylcellulose acetate succinate (HPMCAS), methacrylic acid and ethyl acrylate copolymers, methacrylic acid and ethyl acrylate copolymer, methacrylic acid and methyl methacrylate copolymers (1:1 ratio), methacrylic acid and methyl methacrylate copolymers (1:2 ratio), Polyvinyl acetate phthalate (PVAP) and Shellac resins. Particularly preferred polymers include shellac, anionic copolymers based on methyl acrylate, methyl methacrylate and methacrylic acid, and methacrylic acid and methyl methacrylate copolymers (1:2 ratio). Ideally, the polymer dissolves at a pH equal to 6.0 and above, preferably 6.5 and above.

In another embodiment, a further coating is provided between the core and the external pH-dependent layer. The intermediate coating can be formed from a variety of polymers, including pH-dependent polymers, pH-independent water soluble polymers, pH-independent insoluble polymers, and mixtures thereof.

Representative pH-dependent polymers include shellac type polymers, anionic copolymers based on methylacrylate, methylmethacrylate and methacrylic acid, methacrylic acid and ethyl acrylate copolymer, hydroxypropyl methylcellulose phthalate (HPMCP), and hydroxypropylmethylcellulose acetate succinate (HPMCAS), Representative pH-independent water soluble polymers include PVP or high molecular weight cellulose polymers such as hydroxypropylmethylcellulose (HPMC) or hydroxypropylcellulose (HPC).

Representative pH-independent insoluble polymers include ethylcellulose polymers or ethyl acrylate methyl methacrylate copolymer.

In one aspect of this embodiment, the polymer layer that dissolves in a pH-independent manner includes at least one cellulose-derivative selected from the group consisting of hydroxypropylcellulose or ethylcellulose. In another aspect of this embodiment, the polymer layer that dissolves in a pH-independent manner is made of a 1:9 to 9:1, preferably 2:8 to 3:7, mixture of methacrylic acid and ethyl acrylate copolymer and ethyl acrylate methyl methacrylate copolymer.

The formulations can be used to eliminate or reduce the side effects in the intestine, in particular in the colon, of pharmaceutical agents. It aims in particular at eliminating or reducing the side effect of pharmaceutical agents that are administered as a treatment for a disorder, but that have side effects when they reach the late ileum, the caecum or the colon. For example, the formulations can eliminate or reduce the antibiotic-associated adverse effects of antibiotic agents, eliminate diarrhea, or eliminate the emergence of antibiotic resistance. The formulations can also eliminate a wide variety of pharmaceutical agents such as, but not only, those mentioned in the following detailed description. The formulations can be administered simultaneously with an antibiotic or another pharmaceutical agent.

The formulations can also eliminate or reduce the effects of bacterial or fungal toxins, such as mycotoxins, endotoxins or enterotoxins, or those produced by *Clostridium difficile* in the intestine and/or the colon.

The formulations can also reduce flatulence, stool smell, halitosis or food intolerance, in particular in a pet or in a farm animal.

Methods of preparing the formulations are also disclosed.

Further object and applications will become apparent in the following detailed description of the invention.

DETAILED DESCRIPTION

Figure 1:
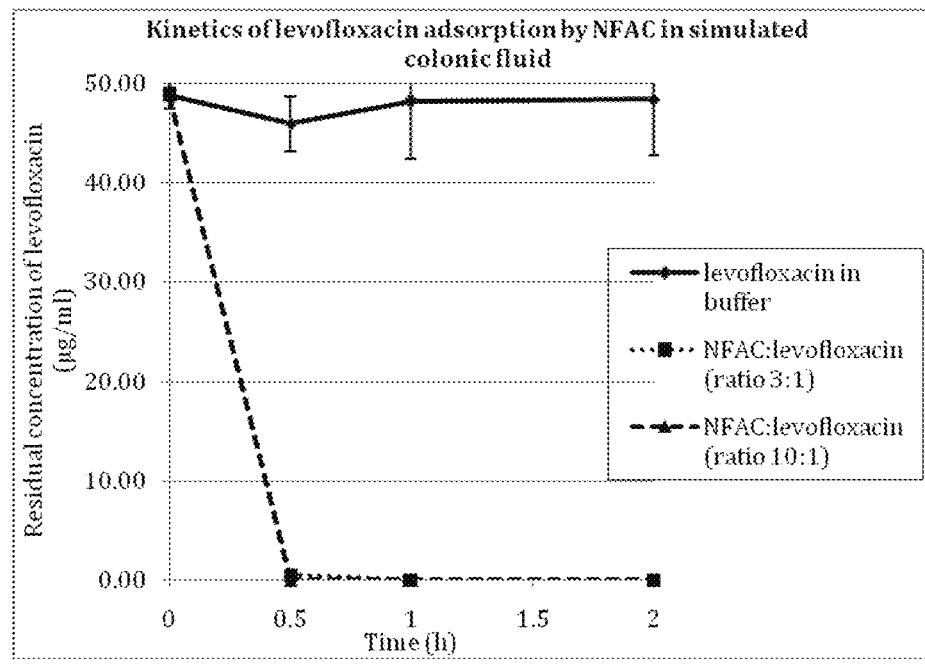
FIG. 1: kinetics of levofloxacin adsorption by NFAC (non-formulated activated charcoal) in simulated colonic fluid.

The invention relates to a formulation including a carrageenan and an adsorbent. The formulation is suitable for oral administration of an adsorbent and delivery of said adsorbent in the lower part of the intestine, i.e. in the late ileum, the caecum and/or the colon. In one embodiment, the carrageenan and adsorbent are present as a mixture, which mixture can be compressed to form a core (the core being further herein referred to as a particle or pellet).

The core can be coated with one or more coating layers, and the coated or uncoated cores can be used to form a drug delivery vehicle, such as a tablet, capsule, pill, and the like.

The formulations of the invention are solid dosage forms useful for delivering an adsorbent to a desired part of the intestine, advantageously in the late ileum, the caecum or the colon. The external and/or intermediate coatings are in particular provided to minimize (preferably to totally prevent) the impact of the adsorbent on the normal absorption process of a therapeutic agent (for example, an antibiotic) by the host organism when said therapeutic agent is administered orally along with the formulation according to the invention. In addition or alternatively, the adsorbent thus formulated is prevented from non-specifically adsorbing material present in the gastrointestinal tract all the way to the terminal part of the small intestine. This results in the release of a non saturated adsorbent, fully or almost fully efficient adsorbent in the specific part of the intestine where its action is needed.

Methods of preparing the formulations, and methods of treatment using the formulations, are also disclosed. The individual components of the formulations are described in detail below.

Antibiotics

The term "antibiotic" denotes a substance that kills or inhibits the growth of microorganisms such as bacteria, fungi, or protozoans. Representative non limiting antibiotics that can be adsorbed according to the invention include Beta-lactams such as Amoxicillin, Ampicillin, Piperacillin, Cephalexin, Cefixime, Ceftazidime, Cefuroxime, Ceftriaxone, Cefotaxime, Ceftiofur, Cefdinir, Cefpodoxime, Cefpirome, Cefquinome, Cefepime, Ceftobiprole, Ceftarolime, Ceftiofur, Imipenem, Ertapenem, Doripenem, Meropenem and beta-lactmase inhibitors such as Clavulanate, Sulbactam or Tazobactam either alone, or given in combination with other beta-lactam antibiotics; Tetracyclines such as Chlortetracycline, Oxytetracycline, Tetracycline, Doxycycline or Minocycline; Macrolides such as Tylosine, Erythromycin, Azithromycin, Clarithromycin, Roxithromycin, Telithromycin, Josamycin, Oleandomycin, Spiramycin, Clindamycin, Lincomycin, Quinupristin or Dalfopristin; Fluoroquinolones such as Nalidixic acid, Ciprofloxacine, Norfloxacin, Ofloxacin, Levofloxacin, Moxifloxacin, Enrofloxacin, Sarafloxacin or Marbofloxacin; Sulfonamides such as Sulfamethoxazole, Sulfadiazine or Sulfathiazole; the dihydroflate reductase inhibitor Trimetoprim; the oxazolodinone antibiotic Linezolid; or other antibiotics such as Florfenicol, Tiamulin or Tigecycline.

Adsorbents

Examples of suitable adsorbents include activated charcoal, clays, including bentonite, kaolin, montmorrillonite, attapulgite, halloysite, laponite, and the like, silica, including colloidal silica (Ludox® AS-40 for example), mesoporous silica (MCM41), fumed silica, zeolites and the like, talc, cholesteramine and the like, polystyrene sulfonates and the like, mono and polysulfonated resins, and any other resins of interest such as those used for bacteriologic testing such as BACTEC® resins. Among these adsorbents, it can be preferred to use those of pharmaceutical grade, such as activated charcoal USP (Merck, France or other sources), kaolin (VWR, France), attapulgite (Lavollee, France), bentonite (Acros Organics, France), Talc USP (VWR, France).

The amount of adsorbent to produce a single dosage form may vary depending upon the host being treated and the overall capacity and selectivity of the adsorbent towards the antibiotic(s). The amount of adsorbent to produce a single dosage form will generally be that amount of the compound which produces a desired effect. The desired effect may be a therapeutic effect, for example a therapeutically significant decrease in the amount of the antibiotic, metabolite thereof, bacterial toxin, or other compound which causes adverse effects in the terminal parts of the gut, in particular in the colon, as compared to when the formulation is not administered.

The amount of the adsorbent will range from about 1% to about 99% by weight of the total pellet, preferably from about 50% to about 95%, most preferably from about 65% to about 95%, in particular from about 80% to about 95% by weight of the core formulation.

In a particular embodiment, activated charcoal is used. In one aspect of this embodiment, activated charcoal preferentially has a specific area above 1500 $m^2/g$, preferentially above 1600 $m^2/g$ and best above 1800 $m^2/g$.

Carrageenan

Carrageenan is a naturally-occurring family of linear sulphated polysaccharides which are extracted from red seaweeds. It is a high molecular weight polysaccharide made up of repeating galactose and 3,6-anhydrogalactose (3,6-AG) units, both sulfated and non-sulfated. The units are joined by alternating alpha 1-3 and beta 1-4 glycosidic linkages. Three basic types of carrageenan are available commercially, i.e. kappa, iota, and lambda carrageenans, which differ by the number and position of the ester sulfate groups on the galactose units.

In one embodiment, the carrageenan can be selected from kappa, iota and lamba carrageenans, and mixtures thereof. In one aspect of this embodiment, the adsorbent is mixed with kappa-carrageenan. In a particular embodiment, the mixture comprises activated charcoal and kappa-carrageenan.

Preferably, the amount of carrageenan is between about 5% and about 25%, more preferably between about 10% and about 20%, by weight of the mixture of the adsorbent with the carrageenan. According to a specific embodiment of the invention, the amount of carrageenan is about 15% by weight of the mixture. For example, the mixture may contain 85% of an adsorbent and 15% of carrageenan, by weight of the total mixture. The possibility of formulating such important amounts of adsorbent with carrageenan was unexpected, and allows delivery of large amounts of adsorbent, preferably of activated charcoal, in the desired part of the gut.

According to a particular embodiment of the invention, a mixture of activated charcoal and carrageenan is provided with the weight ratio indicated above.

The core (or pellet) may be produced by any suitable means known to the skilled artisan. In particular, granulation techniques are adapted to produce said core. For example, the core may be obtained by mixing the adsorbent and the carrageenan in the ratio indicated above, adding a solvent such as water to proceed to wet granulation, followed by extrusion spheronization or one-pot pelletization. Any remaining water can be removed, for example, by drying using conventional techniques the resulting pellets.

In one embodiment, the core, or pellet, of the invention has an average weight particle size in the range from 250 to 3000 μm, in particular 500 to 3000 μm. Several representative size ranges can be preferred. For example, the core size can be comprised between 500 and 1000 μm, or between 800 and 1600 μm. In the context of the present invention, the weight average particle size is determined by sieving different fractions in size, weighting the fractions and calculating the average particle size from the weights. The method is well known to a skilled person in the field of the invention.

It has unexpectedly been found that the mixture of an adsorbent, in particular activated charcoal, and carrageenan has good formulation properties, including:
suitable flow characteristics which allows mass transport during extrusion process,
self lubricating properties with limited sticking to material,
sufficient rigidity to keep the shape of the extrudate,
firmness of the extrudate and enough brittleness which allows smooth cutting of the extrudate, and
minimum plasticity, which allows good spheronization.

None of these advantageous properties has been reported in the prior art.

The invention thus also relates to a composition comprising a mixture of an adsorbent, preferably activated charcoal, with carrageenan (in particular kappa-carrageenan). In a further embodiment, said mixture is in the form of a particle (a compact mixture obtainable, for example, by an extrusion spheronization process), also termed a pellet in the present application.

Those skilled in the art will recognize that the core composition can further include conventional excipients such as antiadherents, binders, fillers, diluents, flavours, colours, lubricants, glidants, preservatives, sorbents and sweeteners. The amounts of such excipients can vary, but will typically be in the range of 0.1 to 50% by weight of the pellet. Of course, the person skilled in the art will adapt these amounts so that the added excipient does not negatively impact on the advantageous properties of the mixture of carageenan with the adsorbent.

External Enteric Coating

The core of the formulation can be layered with a coating such that the drug is released from the formulation in a desired part of the intestine. Several systems are known to those skilled in the art for delivery of an agent to the different parts of the intestine. A comprehensive review of the different systems that can be implemented is provided in Pinto et al., Int J Pharm. 2010 Aug. 16; 395(1-2):44-52.

In a particular embodiment of the invention, the core of the formulation can be layered with a coating such that the drug is released from the formulation in the lower part of the intestine, i.e in the late ileum, caecum and/or colon. Any coating can be used which ensures that the formulation will not release the adsorbent until it is in the desired part of the intestine, namely in the late ileum, the caecum or the colon. The coating may be selected from coatings which are pH-sensitive, redox-sensitive or sensitive to particular enzymes or bacteria. Enteric coatings are well known to those skilled in the art (for example, reference is made to Chourasia M K and Jain S K, "Pharmaceutical approaches to colon targeted drug delivery systems", J Pharm PharmaceutSci 6(1): 33-66, 2003).

Preferred coating materials are those which are pH sensitive, i.e. pH-dependent enterosoluble polymers. As will be apparent in the following parts of the application, the choice of the pH-dependent enterosoluble polymer can be made by taking into account the pH profile of the gastro intestinal tract of the mammal who will be the recipient of the treatment (also herein referred to as the "host being treated").

The term "enterosoluble polymer" denotes a polymer that is stable and does not dissolve in the stomach and the upper parts of the gastrointestinal tract, but readily dissolves when it arrives at the desired part of the gut to release the active material contained therein. The solubility of a pH-dependent enterosoluble polymer depends on the conditions of acidity or alkalinity found all along the gut.

In a particular embodiment, the pH-dependent enterosoluble polymer can be selected among cellulose acetate trimellitate (CAT), cellulose acetate phthalate (CAP) such as Aquateric®, anionic copolymers based on methylacrylate, methylmethacrylate and methacrylic acid such as Eudragit® FS30D, Hydroxypropyl methylcellulose phthalate (HP-MCP), Hydroxypropylmethylcellulose acetate succinate (HPMCAS) LF, LG, MF, MG or HF Grades such as Aqoat®, methacrylic acid and ethyl acrylate copolymers such as Eudragit® L100-55, methacrylic acid and ethyl acrylate copolymer such as Eudragit® L30D-55, methacrylic acid and methyl methacrylate copolymers (1:1 ratio) such as Eudragit® L-100 and Eudragit® L12,5, methacrylic acid and methyl methacrylate copolymers (1:2 ratio) such as Eudragit® S-100 and Eudragit® S12,5, Polyvinyl acetate phthalate (PVAP) such as Sureteric® and Opadry® and Shellac resins such as SSB® Aquagold.

In a preferred embodiment, the pH-dependent enterosoluble polymer used in the external layer dissolves at a pH equal to 6.0 and above. Even more preferably, it dissolves at a pH equal to 7.0 and above. In this context, the polymer may in particular be selected in the group consisting of shellac such as SSB® Aquagold, anionic copolymers based on methyl acrylate, methyl methacrylate and methacrylic acid such as Eudragit® FS30D, methacrylic acid and methyl methacrylate copolymers (1:2 ratio) such as Eudragit® S-100 and Eudragit® S12,5, HPMCAS such as Aqoat® AS-MF, MG or HF grades or hydroxypropyl methylcellulose phthalate (HPMCP) such as HP-55 grade.

The above referred to Eudragit® copolymers are commercialized by Evonik. Their composition is known to the skilled artisan and may be found, in particular, in US 2008/0206350 (U.S. Ser. No. 12/034,943).

The pH dependent enterosoluble polymer is selected first for its ability to resist acidic pH found into the upper part of the gastro-intestinal tract (GIT) of most mammals and second to fulfill requirement of delivering the active agent into the lower part of the intestine, i.e. preferentially the late ileum, the caecum or the colon.

The person skilled in the art knows that in many mammals, the physiology of the GIT can vary both in terms of pH, length, and transit time. Table 1 below represents the various physiological characteristics of some mammals.

TABLE 1

Various intestinal pH found in the gut of different mammals

| Species | Stomach pH Anter-poster | Small intestine pH upper-lower | Caecum pH | Colon pH |
| --- | --- | --- | --- | --- |
| Man | 1.7-5.0 | 5.6-7.5 | 5.9 | 5.5/7 |
| Pig | 4.3-2.2 | 6.0-7.5 | 6.3 | 6.8 |
| Dog | 5.5-3.4 | 6.2-7.5 | 6.4 | 6.5 |
| Cat | 5.0-4.2 | 6.2-7.6 | 6.0 | 6.2 |
| Horse | 5.4-3.3 | 6.7-7.9 | 7.0 | 7.4 |
| Poultry | 4.9-4.2 | 5.8-7.7 | 7.0 | ND |

From KararliTT., *Biopharm Drug Dispos.* 1995 Jul; 16(5): 351-80. *Comparison of the gastrointestinal anatomy, physiology, and biochemistry of humans and commonly used laboratory animals*. Stevens C. E., and Hume, I. D. 1995. *Comparative Physiology of the Vertebrate Digestive System*. 2nd ed. New York: Cambridge University Press.

It can be seen from table 1 that most of the enterosoluble polymers will begin to dissolve in the upper part of the small intestine and, thanks to the thickness of the external coating, the adsorbent will be released into the lower part of the intestine by the time dissolution is achieved.

The coating thickness can be adapted to finely tune the release of the adsorbent into the desired part of the intestine. For example, the enterosoluble polymer layer can represent from 10% to 40% in weight of the weight of the total formulation. In a preferred embodiment, the amount of enterosoluble layer is at least 15% of the total weight of the formulation. In a preferred embodiment, the enterosoluble polymer layer represents from about 15% to about 35% by weight of the total formulation, even more preferably, from about 15% to about 20%. In a particular embodiment, the enterosoluble polymer layer is present in the formulation in an amount of about 15% by weight of the total formulation.

The type and/or amount of enterosoluble polymer which can be used to coat the core of the invention may be selected by using the Biodis dissolution tester (USP III release apparatus) as provided in the examples.

The pH-dependent enterosoluble coating can also include various combinations of different pH-dependent enterosoluble polymers. Those skilled in the art are able to select such mixtures of pH-dependent polymers taking into account their general knowledge in this field. For example, as mentioned in the above cited article of Chourasia and Jain, a combination of two methacrylic acid polymers such as Eudragit® L100-55 and Eudragit® S100 can be provided around the core of the invention.

In a particular embodiment of the invention, the external coating contains Eudragit FS30D, or a mixture of Eudragit FS30D and Eudragit L30D-55 in a weight ratio comprised in particular between 99:1 to 80:20 (FS30D:L30D-55).

In a particular embodiment, the pH-dependent enterosoluble polymer is selected from
  shellac,
  anionic copolymers based on methyl acrylate, methyl methacrylate and methacrylic acid,
  mixtures of methyl methacrylate and methacrylic acid such as Eudragit® FS30D and methacrylic acid and ethyl acrylate copolymer such as Eudragit® L30D-55, in a ratio comprised between 99:1 and 80:20, and
  methacrylic acid and methyl methacrylate copolymers (1:2 weight ratio).

In a further particular embodiment, the formulation according the invention comprises:
  a core containing a mixture of activated charcoal with carrageenan (preferably kappa carrageenan), and
  a layer of an anionic copolymer based on methyl acrylate, methyl methacrylate and methacrylic acid, such as Eudragit® FS30D.

In a further particular embodiment, the formulation according the invention comprises:
  a core containing a mixture of activated charcoal with carrageenan (preferably kappa carrageenan), and
  a layer of a mixture of methyl methacrylate and methacrylic acid such as Eudragit® FS30D and methacrylic acid and ethyl acrylate copolymer such as Eudragit® L30D-55, in a ratio comprised between 99:1 and 80:20.

In another particular embodiment, the formulation according the invention comprises
  a core containing a mixture of activated charcoal with carrageenan (preferably kappa carrageenan), and
  a layer of shellac.

The external enterosoluble layer may be applied onto the core by any suitable means known to a person skilled in the art. For example, it can be applied using classical fluid bed technology where a water-based or solvent-based solution of coating is applied by spray-drying onto the core pellet. When the weight gain is reached, the formulation can be dried and a further coating can be applied. Multiple coatings can thus be applied successively using spray drying technology.

Furthermore, the colonic region has a high presence of microbial anaerobic organisms providing reducing conditions. Thus the external coating may suitably comprise a material which is redox-sensitive. Such coatings may comprise azopolymers which can for example consist of a random copolymer of styrene and hydroxyethyl methacrylate, cross-linked with divinylazobenzene synthesized by free radical polymerization, the azopolymer being broken down enzymatically and specifically in the colon, or disulphide polymers (see PCT/BE91/00006).

Other materials providing release in the colon are amylose, for example a coating composition can be prepared by mixing amylose-butan-1-ol complex (glassy amylose) with Ethocel aqueous dispersion (Milojevic et al., Proc. Int. Symp. Contr. Rel. Bioact. Mater. 20, 288, 1993), or a coating formulation comprising an inner coating of glassy amylose and an outer coating of cellulose or acrylic polymer material (Allwood et al GB 9025373.3), pectin, a polysaccharide which is degraded by colonic bacterial enzymes (Ashford et al., Br Pharm. Conference, 1992, Abstract 13), reticulated into a gel by divalent cations such as calcium (Rubenstein et al., Pharm. Res., 10, 258, 1993) or zinc (El-Gibaly, Int. J. Pharmaceutics, 232, 199, 2002), chondroitin sulphate (Rubenstein er awl., Pharm. Res. 9, 276, 1992) and resistant starches (Allwood et al., PCT WO 89/11269, 1989), dextran hydrogels (Hovgaard and Brondsted, 3rd Eur. Symp. Control. Drug Del., Abstract Book, 1994, 87) modified guar gum such as borax modified guar gum (Rubenstein and Gliko-Kabir, S.T.P. Pharma Sciences 5, 41-46, 1995), P-cyclodextrin (Siekeer al., Eu. J. Pharm. Biopharm. 40 (suppl), 335, 1994), saccharide containing polymers by which a polymeric construct is included comprising a synthetic oligosaccharide-containing biopolymer including methacrylic polymers covalently coupled to oligosaccharides such as cellobiose, lactulose, raffinose, and stachyose, or saccharide-containing natural polymers including modified mucopolysaccharides such as cross linked chondroitin sulfate; methacrylate-galactomannan (Lehmann and Dreher, Proc. Int. Symp. Control. Rel. Bioact. Mater. 18, 331, 1991) and pH sensitive hydrogels (Kopecek et al., J. Control. Rel. 19, 121, 1992). Resistant starches, eg glassy amylose, are starches that are not broken down by the enzymes in the upper gastrointestinal tract but are degraded by enzymes in the colon.

Intermediate Coating

According to a particular embodiment of the invention, the formulation described above comprises at least one further coating provided between the core and the external enteric coating. This further layer(s) (also referred to as "intermediate coating") is provided to further delay the release of the adsorbent when necessary. The intermediate coating is in particular provided to minimize (preferably to totally prevent) the impact of the adsorbent on the normal absorption process of a therapeutic agent (for example, an antibiotic) by the host organism when said therapeutic agent is administered orally along with the formulation according to the invention. This embodiment is particularly suited to the case where the administered therapeutic agent has a delayed absorption profile, as a consequence of the time necessary to achieve maximum concentration of the agent into the blood ($T_{max}$).

According to a particular embodiment, the intermediate coating is provided onto the core of the invention, and a further coating is applied with a pH-dependent enterosoluble polymer, such as Eudragit™ FS30D (as explained above) or a mixture Eudragit® FS30D and Eudragit® L30D-55, in a ratio comprised between 99:1 and 80:20. The pH-dependent enterosoluble polymer protects the core from the acidic environment found in the upper part of the gastro-intestinal tract. Once the pH-dependent polymer is dissolved, further delayed release of the adsorbent can be obtained due to the intermediate coating.

The intermediate coating can contain pH-dependent or pH-independent polymers.

Among the pH-dependent polymers that can be used as intermediate coating, examples include those described above in "external enterosoluble layer" part, and in particular shellac type polymers such as SSB® Aquagold, anionic copolymers based on methyl acrylate, methyl methacrylate and methacrylic acid such as Eudragit® FS30D, methacrylic acid and ethyl acrylate copolymer such as Eudragit® L30D-55, HPMCAS such as Aqoat AS-MF, MG or HF grades or hydroxypropyl methylcellulose phthalate (HPMCP) such as HP-55 grade. In a particular embodiment, the intermediate coating can be a mixture of pH-dependent polymers such as Eudragit® FS30D and Eudragit® L30D-55, in a ratio comprised between 99:1 and 80:20 pH-independent polymers can be selected among slowly water soluble polymers and water insoluble polymers. Non limiting examples of pH-independent water soluble polymers include Polyvinylpyrolidone (PVP) and high molecular weight cellulose polymers such as hydroxypropylmethylcellulose (HPMC), hydroxypropyl cellulose (HPC). Further non limiting examples of pH-independent insoluble polymers include ethylcellulose polymers and ethyl acrylate methyl methacrylate copolymer (such as Eudragit® NE30D).

In a particular embodiment of the invention, the intermediate coating contains a mixture of polymers. In a first alternative, the mixture of polymers comprises polymers of the same type. For example, the mixture can comprise a pH-dependent polymer with another pH-dependent polymer, a pH-independent soluble polymer with another pH-independent soluble polymer, or a pH-independent insoluble polymer with another pH-independent insoluble polymer. In another alternative, the mixture of polymers comprises polymers of different types. The mixture can comprise a pH-dependent polymer with a pH-independent polymer (either water soluble or insoluble), a pH-independent soluble polymer with a pH-independent insoluble polymer, or a pH-dependent polymer with a pH-independent soluble polymer and a pH-independent insoluble polymer. For example, the intermediate coating can comprise the mixture of a pH-dependent polymer with a pH-independent polymer, such as a mixture of Eudragit® L30D55 with Eudragit® NE30D (for example, in a weight ratio between about 1:9 and about 9:1, in particular between about 2:8 and about 3:7).

The preferred coating and coating component weight ratio can be readily determined by those skilled in the art, for example, by evaluating the release profile of the dosage form, as provided in the examples (e.g. see Example 8).

For a pharmaceutical agent given by oral route, for example an antibiotic, which has a $T_{max}$ between about 1 and about 2 hours (such as ciprofloxacin), the core according to the invention can be coated with a single pH-dependent polymer, such as an anionic copolymer based on methylacrylate, methylmethacrylate and methacrylic acid (such as Eudragit® FS30D). Release of the adsorbent is achieved in vitro and in vivo (in particular in a human subject) after about 4-6 hours, which limits the interaction of the adsorbent with the normal absorption process of the antibiotic, or another pharmaceutical agent. The same type of formulations can be administered after parenteral administration of the antibiotic, where residual antibiotic is found in the gastrointestinal tract after bile or intestinal membrane excretion. In this case, there is no risk of interaction of the adsorbent with the absorption process of the antibiotic.

In the case where pharmaceutical agents with delayed absorption ($T_{max}$ above 2 hours), and in particular antibiotics such as third generation cephalosporins, are given by oral route concomitantly with the adsorbent material formulated in a delayed delivery system such as those described above, it may be preferable to further delay the release of the adsorbent. This can be achieved, for example, by primarily coating the core with between about 1 and about 3% ethylcellulose (w/w of the total formulation), preferably 1.5-2.5% (w/w of the total formulation), more preferably with 2% ethylcellulose or a mixture of Eudragit® L30D-55 with Eudragit® NE30D (between 10-40%, preferably between 15-35% w/w of the total formulation) further coated with at least 15% (w/w of the total formulation) of Eudragit® FS30D.

In a particular embodiment, the intermediate coating is selected in order to achieve a delay of about 20 minutes to about 2 hours in the release of the adsorbent, as measured by in vitro testing such as with a BioDis dissolution tester (USP III release apparatus). In this system, the dosage form is successively placed into glass tubes filled with approx 200 mL of dissolution media with a composition yielding pH, buffer capacity and osmolarity corresponding to the different sections of the gastrointestinal tract, such as described by Jantratid et al. in *Pharm. Res.* 25 (2008), 1663-1676. This allows a good simulation of in vivo release before testing into mammals. pH, fed vs fasted state, and various other physiological conditions can be tested. Using the BioDis system, it is possible for those skilled in the art to finely tune the formulation to achieve a desired pre-determined delayed release.

According to the above, a particular embodiment of the invention relates to a formulation comprising:
  a core comprising a mixture of an adsorbent with carrageenan,
  an external layer of a pH-dependent enterosoluble polymer, and
  a intermediate coating provided between the core and the external layer.

In a particular embodiment, the invention relates to a formulation comprising:
  a core comprising a mixture of activated charcoal with carrageenan (preferably kappa-carrageenan),
  a intermediate coating selected in the group consisting of HPMC, ethylcellulose and a mixture of methacrylic acid and ethyl acrylate copolymer such as Eudragit® L30D-55 and ethyl acrylate methyl methacrylate copolymer such as Eudragit® NE30D (for example in a mixture ratio of 1:9 to 9:1, preferably of 2:8 to 3:7), and
  an external layer of an anionic copolymer based on methyl acrylate, methyl methacrylate and methacrylic acid, such as Eudragit® FS30D.

In another particular embodiment, the formulation of the invention comprises:
  a core comprising a mixture of activated charcoal with carrageenan (preferably kappa-carrageenan),
  a 1-3% ethylcellulose intermediate coating, preferably a 1.5-2.5% ethylcellulose coating, most preferably a 2% ethylcellulose intermediate coating (w/w of the total formulation), and
  a 15% (w/w of the total formulation) external layer of an anionic copolymer based on methyl acrylate, methyl methacrylate and methacrylic acid, such as Eudragit® FS30D.

In a further particular embodiment, the formulation of the invention comprises:
  a core comprising a mixture of activated charcoal with carrageenan (preferably kappa-carrageenan),
  a 15-35% (w/w of the total formulation) intermediate coating made of a 2:8 to 3:7 mixture of methacrylic acid and ethyl acrylate copolymer (such as Eudragit® L30D-55) and ethyl acrylate methyl methacrylate copolymer (such as Eudragit® NE30D), and
  a 15% (w/w of the total formulation) external layer of an anionic copolymer based on methyl acrylate, methyl methacrylate and methacrylic acid, such as Eudragit® FS30D.

In another particular embodiment, the formulation of the invention comprises:
  a core comprising a mixture of activated charcoal with carrageenan (preferably kappa-carrageenan),
  a 1-3% ethylcellulose intermediate coating, preferably a 1.5-2.5% ethylcellulose coating, most preferably a 2% ethylcellulose intermediate coating (w/w of the total formulation), and
  a 15% to 35% (w/w of the total formulation) external layer of a mixture of methyl methacrylate and methacrylic acid such as Eudragit® FS30D and methacrylic acid and ethyl acrylate copolymer such as Eudragit® L30D-55, in a ratio comprised between 99:1 and 80:20.

In a further particular embodiment, the formulation of the invention comprises:
  a core comprising a mixture of activated charcoal with carrageenan (preferably kappa-carrageenan),
  a 15-35% (w/w of the total formulation) intermediate coating made of a 2:8 to 3:7 mixture of methacrylic acid and ethyl acrylate copolymer (such as Eudragit® L30D-55) and ethyl acrylate methyl methacrylate copolymer (such as Eudragit® NE30D), and
  a 15% to 35% (w/w of the total formulation) external layer of a mixture of methyl methacrylate and methacrylic acid such as Eudragit® FS30D and methacrylic acid and ethyl acrylate copolymer such as Eudragit® L30D-55, in a ratio comprised between 99:1 and 80:20.

Dosage Forms

In another aspect, the present invention provides pharmaceutically acceptable dosage forms which comprise a therapeutically-effective amount of one or more of the adsorbents described above, formulated together with carrageenan and one or more pharmaceutically acceptable additives. As described in detail below, the dosage forms of the invention can be specially formulated for administration in solid form.

The phrase "therapeutically-effective amount" as used herein means that amount of one or more of the compounds described above, material, or formulation comprising one or more of the compounds described above which is effective for producing some desired therapeutic effect.

The phrase "pharmaceutically acceptable" is employed herein to refer to those compounds, materials, formulations, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable additive" as used herein means a pharmaceutically-acceptable material, formulation or vehicle, such as a solid filler, diluent, excipient involved in carrying or transporting the subject compound from one organ, or portion of the body, to another organ, or portion of the body. Each additive must be "acceptable" in the sense of being compatible with the other ingredients of the formulation and not injurious to the patient.

Dosage forms that contain multiple units, such as pellets individually coated by enterosoluble polymers such as the one described above, can be preferred in order to improve the in vivo dispersion of the activated charcoal. Such pellets present more practical flexibility, because coating can be directly achieved on their surface, for example, using a fluid bed system.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the dosage form.

Dosage forms of the present invention include those suitable for oral administration. The formulations can conveniently be presented in unit dosage form and can be prepared by any methods well known in the art of pharmacy.

Dosage forms of the invention suitable for oral administration can be in the form of capsules, tablets, sachets, each containing a predetermined amount of the adsorbent formulation.

A tablet can be made by compression or molding, optionally with one or more accessory ingredients. Compressed tablets can be prepared using binder (for example, gelatin or hydroxypropylmethyl cellulose), lubricant, inert diluent, preservative, disintegrant (for example, sodium starch glycolate, cross-linked sodium carboxymethyl cellulose or polysaccharide), surface-activated or dispersing agent. Molded tablets can be made by molding in a suitable machine a mixture of the powdered compound moistened with an inert liquid diluent such as water.

The solid dosage forms described above can be combined in a final dosage form comprising single or multiple units. Examples of multiple units include multilayer tablets, capsules containing tablets, pellets, granules, etc.

The core of the invention can be coated with an external layer, and optionally an intermediate coating as provided above. The coated formulation (coated with an external enteric coating, and comprising or not an intermediate coating) or uncoated core can further be combined in a unit drug dosage form, such as a tablet, capsule, and the like, which can be further coated with a coating material for effective delayed-release which include, but are not limited to, cellulosic polymers such as hydroxypropyl cellulose, hydroxyethyl cellulose, hydroxymethyl cellulose, hydroxypropyl methyl cellulose, methylcellulose, carboxymethylcellulose sodium, copolymers such as polyvinyl pyrrolidone; hydroxypropyl methyl cellulose acetate succinate, hydroxypropylmethyl cellulose phthalate, cellulose acetate phthalate, cellulose acetate trimellitate and acrylic acid polymers and copolymers, preferably formed from acrylic acid, methacrylic acid, methyl acrylate, ethyl acrylate, methyl methacrylate and/or ethyl methacrylate, and other methacrylic resins that are commercially available under the tradename Eudragit®. (Rohm Pharma; Westerstadt, Germany), including Eudragit® L30D-55 and L100-55 (soluble at pH 5.5 and above), Eudragit® L-100 (soluble at pH 6.0 and above), Eudragit® S (soluble at pH 7.0 and above, as a result of a higher degree of esterification), and Eudragit FS30D a anionic copolymer of methacrylic acid, methyl acrylate and methylmethacrylate; ethyl cellulose, cellulose acetate; Eudragit® NE, RL and RS (water-insoluble polymers having different degrees of permeability and expandability) vinyl acetate, vinylacetate phthalate, vinylacetate-crotonic acid copolymer, and ethylene-vinyl acetate copolymer; vinyl polymers and; Enzymatically degradable polymers such as azo polymers, pectin, chitosan, amylose and guar gum; zein and shellac.

The preferred coating weights for particular coating materials can be readily determined by those skilled in the art by evaluating individual release profiles for tablets, pellets and granules prepared with different quantities of various coating materials.

It is the combination of materials, method and form of application that produce the desired release characteristics.

The coating formulation can include conventional additives, such as plasticizers, pigments, colorants, stabilizing agents, glidants, etc. A plasticizer is normally present to reduce the fragility of the coating, and will generally represent about 5 wt. % to 50 wt. % relative to the dry weight of the polymer. Examples of typical plasticizers include polyethylene glycol, propylene glycol, triacetin, dimethyl phthalate, diethyl phthalate, dibutyl phthalate, dibutylsebacate, triethyl citrate, tributyl citrate, triethyl acetyl citrate, castor oil and acetylated monoglycerides. A stabilizing agent is preferably used to stabilize particles in the dispersion. Typical stabilizing agents are nonionic emulsifiers such as sorbitan esters, polysorbates and polyvinylpyrrolidone. Glidants are recommended to reduce sticking effects during film formation and drying, and will generally represent approximately 0 wt. % to 100 wt. % of the polymer weight in the coating solution. One effective glidant is talc. Other glidants such as magnesium stearate and glycerol monostearates can also be used. Pigments such as titanium dioxide can also be used. Small quantities of an anti-foaming agent, such as a silicone (e.g., simethicone), can also be added to the coating formulation.

These dosage forms can be administered to humans and animals for therapy by any suitable route of administration.

Actual dosage levels of the adsorbent in the dosage form of this invention can be varied so as to obtain an effective removal of any residual antibiotic or other pharmaceutical agents or toxin in the intestinal tract, for a particular patient, formulation, and mode of administration, without being toxic to the patient.

The selected dosage level will depend upon a variety of factors including the activity of the particular compound of the present invention employed, the time of administration, the rate of excretion or metabolism of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical formulation required. For example, the physician or veterinarian could start with doses of the compounds of the invention employed in the pharmaceutical formulation at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above.

If desired, the effective daily dose of the active compound can be administered as two, three, four, five, six or more sub-doses administered separately at appropriate intervals throughout the day, optionally, in unit dosage forms.

As already mentioned, the formulation according to the invention may be used in a method for eliminating the adverse effects of therapeutic agents, in particular, but not only, of antibiotics. According to a particular embodiment of this method, the formulation of the invention and the therapeutic agent are administered simultaneously. As such the amount of adsorbent may be adapted to the amount of therapeutic agent administered to the subject in need thereof. In this case, the weight ratio between the adsorbent and the antibiotic agent may be above 1, more preferably above 2, even more preferably above 3, and most preferably above 9.

The term "treatment" is intended to encompass also prophylaxis, therapy and cure.

The subject receiving this treatment is any animal in need, including primates, in particular humans, and other mammals such as equines, cattle, swine and sheep; poultry and pets in general may also be recipients of such a treatment.

The administration of the formulation according to the invention to an animal is preferably carried out by including it in the animal's food. This is preferably accomplished by preparing an appropriate feed premix containing the formulations according to the invention in an effective amount and incorporating the premix into the complete ration. Accordingly, the present invention also relates to an animal food premix comprising food and formulations as described above. The invention also relates to an animal food ration comprising the formulations according to the invention.

Applications

Therapeutic Applications:

The formulations according to the invention can be used to treat conditions and disorders for which intestinal delivery of adsorbents is appropriate. Accordingly, the invention also relates to a formulation as described above, for use as a medicament.

The formulation according to the invention can be used to adsorb and therefore remove from the intestine any drug, metabolite or prodrug thereof, or toxin. This may be done after oral or parenteral administration of an active drug, which could be useful for limiting or decreasing adverse effects in the subject being treated when they reach the lower intestine and/or colon.

As such, the present invention relates to the formulation as described above, for use in a method for eliminating drugs in the intestinal tract before they reach the colon or as they reach the colon, preferably before they reach the caecum or as they reach the caecum and proximal colon.

The invention further provides a method for eliminating drugs in the intestinal tract before they reach the colon or as they reach the colon, preferably before they reach the caecum or as they reach the caecum and proximal colon, comprising administering to a patient in need thereof a formulation according to the invention.

Furthermore, the invention provides a formulation as described above, for use in a method for reducing or eliminating the side effect(s) of a drug in the intestinal tract, wherein the formulation eliminates the drug before it reaches the colon or as it reaches the colon, preferably before it reaches the caecum or as it reaches the caecum and proximal colon.

The terms "drug", "therapeutic agent" and "pharmaceutical agent", and terms derived therefrom, are herein used interchangeably and refer to a compound that provides a desired biological or pharmacological effect when administered to a human or animal.

Conditions and disorders that may be treated with the formulation according to the invention may be those that result from exposure of the colon to antibiotics, such as the development of antibiotic resistance, antibiotic treatment-associated development of *C. difficile* (or other pathogenic bacteria), antibiotic treatment-associated fungal infections or antibiotic treatment-associated diarrhea. The adsorbent will adsorb residual antibiotics, and the formulations according to the invention can be administered in a therapeutically effective dosage to a patient who has been, is being, or will be administered an antibiotic. Any antibiotic that can be adsorbed into/onto the adsorbent can be inactivated and has no antibiotic activity once fully adsorbed. Representative examples of antibiotic classes that can be adsorbed include beta-lactams, cyclines, macrolides, quinolones, aminoglycosides, glycopeptides, sulfonamides, phenicols, furans, polypeptides, oxazolidones and antibiotics such as fosfomycin, rifampin and the like.

The invention thus also relates to a formulation as described above, for use in a method for eliminating residual antibiotics in the intestinal tract, preferably before they reach the colon or as they reach the colon. More preferably, the formulation is used in a method for eliminating residual antibiotics in the intestinal tract, preferably before they reach the caecum or as they reach the caecum and proximal colon. According to the invention, the adsorbent is preferably delivered between the part of the intestine where the antibiotics are absorbed (duodenum and jejunum) and where their deleterious effect on the commensal bacteria occur (caecum and colon). The invention further relates to a method for eliminating residual antibiotics in the intestinal tract, preferably before they reach the colon or as they reach the colon, most preferably before they reach the caecum or as they reach the caecum and proximal colon comprising administering to a subject in need thereof an effective amount of the formulation of the invention.

The invention further relates to a formulation as described above, for use in a method for eliminating the adverse effects of antibiotic agents in the intestinal tract, in particular for eliminating the development of antibiotic resistance, antibiotic treatment-associated development of *C. difficile* (or other pathogenic bacteria), antibiotic treatment-associated fungal infections or antibiotic treatment-associated diarrhea. The invention further relates to a method for eliminating the adverse effects of antibiotic agents in the intestinal tract, comprising administering to a subject in need thereof an effective amount of the formulation of the invention.

In another embodiment, the formulation of the invention is administered to a patient who suffers from a disorder treated with pharmaceutical agents which have side effects when they reach the lower part of the intestine, in particular when they reach the colon. As developed below, Irinotecan is a representative compound having such behavior.

In particular embodiments, the formulation is administered to a patient who suffers from a disorder treated with pharmaceutical agents which bind to relevant receptors in the body of the patient other than in the colon to treat the disorder, but which, when bound to receptors in the colon, result in side effects. For example, the colon includes cholinergic and serotonin receptors, which are also present in the central nervous system. Treatment with agents that bind to cholinergic receptors can result in side effects if the compounds bind to receptors in the colon. Co-administration of the formulation of the invention with the agents that bind to such receptors can minimize or eliminate these side effects.

The invention thus also relates to a formulation as described above, for use in a method for eliminating the side effects in the intestine, in particular in the colon, of pharmaceutical agents administered as a treatment for a disorder, but that have side effects when they reach the late ileum, the caecum or the colon. The present invention can alleviate or eliminate these side effects. The invention further relates to a method for eliminating the side effects in the intestine, in particular in the colon, of pharmaceutical agents, in particular pharmaceutical agents administered as a treatment for a disorder, but that have side effects when they reach the late ileum, the caecum or the colon, comprising administering to a subject in need thereof an effective amount of the formulation of the invention. In particular, the present invention can be used to alleviate or eliminate an inflammation and/or diarrhea induced by a treatment with a pharmaceutical agent.

Irinotecan is an illustrative, non-limiting, example of a pharmaceutical agent administered as a treatment for a disorder, but that has side effects when it, and/or its metabolites, reach the late ileum, the caecum or the colon. A particular embodiment of the invention provides a formulation for eliminating or reducing Irinotecan-induced diarrhea, in particular Irinotecan-induced late-onset diarrhea.

Irinotecan (also known as CPT-11), a semi-synthetic analogue of the natural alkaloid camptothecin, is a soluble prodrug of 7-ethyl-10-hydroxycamptothecin (SN-38) which is a topoisomerase I inhibitor which has 1000-fold more potent antineoplastic activity than the prodrug form in vitro. Irinotecan has more particularly been approved by the FDA for metastatic colorectal cancer in 1998. It is mostly used as first line in combination regimens or as a single agent after failure of 5-fluorouracil (5-FU)-based therapy. However, it has been found that late-onset diarrhea is a major dose-limiting toxicity of Irinotecan. Accumulation of SN-38 in the intestine is the main cause of Irinotecan-induced late stage diarrhea.

More generally, diarrhea often develops as a side effect during clinical treatment with chemotherapeutic agents. This adverse effect is most commonly associated with chemotherapeutic agents such as 5-fluorouracil, cisplatin or Irinotecan. In particular, late-onset diarrhea due to the administration of Irinotecan can be persistent, may lead to dehydration and electrolyte imbalance and can be, in some cases, sufficiently serious (grade 3 or 4 diarrhea) that Irinotecan administration must be modified, interrupted or discontinued. Diarrhea constitutes a problematic symptom for patients, and because it may provoke reductions in Irinotecan doses or the frequency of Irinotecan administration, diarrhea may compromise the therapeutic efficacy of Irinotecan which is highly dependent on the administered dose.

A sign of the importance and frequency of this side effect is the fact that a protocol for treatment by loperamide, in case diarrhea occurs, is even indicated on the labeling of Irinotecan. Indeed, in humans, the intensive and immediate administration of loperamide (an agent that slows intestinal motility and affects water and electrolyte movement through the bowel) is used to reduce or control diarrhea once diarrhea has started. However, loperamide has side effects on its own, such as inducing intestinal occlusion (Hanauer, S B, *Rev Gastroenterol Disord.* 8 (2008), 15-20).

The prevention of Irinotecan-induced diarrhea with activated charcoal has been previously proposed (Michael et al., Journal of Clinical Oncology, Vol. 22, No. 21, Nov. 1, 2004). However, the treatment consisted in the oral administration of non-formulated activated charcoal. This raises at least two issues, both related to the non specific nature of this adsorbent. One of these issues is the likely saturation of activated charcoal by digestive material as it progresses through the gastrointestinal tract. It would be preferable to provide to the terminal parts of the intestine a maximally active adsorbent in order to obtain a strong adsorption of Irinotecan and/or its metabolites at the place where they elicit their unwanted effects. The second problem is related to the fact that Irinotecan is often administered within a multi-drug treatment regimen, which may comprise drugs administered orally. In particular, Irinotecan can be administered in association with 5-fluorouracil and leucovorin; other drugs may be added, as required for various reasons, to the treatment. Co-administration of non-formulated charcoal in this context is undesirable since the adsorbent may adsorb the co-administered drug(s) and thus prevent them to elicit the desired effects they have been used for.

The present invention is advantageous in that it allows eliminating or reducing the adverse effects of Irinotecan, in particular Irinotecan-induced diarrhea (most particularly Irinotecan-induced late-onset diarrhea) without eliciting further adverse effects or toxicity. Furthermore, thanks to the present invention, Irinotecan can be used at its most effective therapeutic dose since no alteration of the dosage regimen is necessary because of the elimination of the adverse effects of Irinotecan. In preventing diarrhea symptoms in patients receiving Irinotecan therapy, the formulation of the present invention has the potential to reduce the incidence, severity, and/or duration of diarrhea, improve patient quality of life, avoid diarrhea-related hospitalization, and/or prevent Irinotecan dose reduction, treatment interruption, or discontinuation.

The method of the invention also provides elimination or reduction of metabolites of Irinotecan, in particular SN-38, and the elimination or reduction of the adverse effect of such Irinotecan metabolites.

The person skilled in the art will recognize that these advantages are also provided for therapy with molecules other than Irinotecan, that elicit adverse effects, in particular molecules that induce diarrhea, when they reach the lower part of the gastrointestinal tract. Such molecules could be other analogues and derivatives of camptothecin, such as Topotecan, and other drugs used in cancer chemotherapy.

Colchicine, a drug used for pain and gout arthritis treatment is another representative example of a pharmaceutical agent whose elimination according to the invention would be advantageous.

It is also known that gastrointestinal problems are commonly reported because of adverse drug reactions with blood pressure medications (Calcium Channel blockers), pain medications (especially narcotics), antidepressants, antacids that contain aluminum and calcium, antiparkinson drugs, antispasmodics, diuretics, and anticonvulsants, and that many drug classes are associated with constipation. Often, constipation persists, and patients discontinue treatment because the side effect is burdensome. Drugs such as risperidone can be associated with colonic disorders, such as megacolon (Lim et al, Singapore Med J 2002, Vol 43(10): 530-532). The formulation of the invention can be administered to a patient in need thereof to treat these problems.

Thus, in a particular embodiment, the invention relates to a formulation as described above, for use in a method for eliminating the side effects in the intestine, in particular in the colon, of a therapeutic agent, for example of a chemotherapeutic agent, in particular of Irinotecan and derivatives thereof (in particular its metabolite SN-38). The invention further relates to a method for eliminating the side effects in the intestine, in particular in the colon, of a therapeutic agent, for example of a chemotherapeutic agent, in particular of Irinotecan and derivatives thereof (in particular its metabolite SN-38) when it reaches the late ileum, the caecum or the colon, comprising administering to a subject in need thereof an effective amount of the formulation of the invention.

The invention further relates to a method for treating cancer (in particular metastatic colorectal cancer) with a chemotherapeutic agent, in particular with Irinotecan, comprising administering to a patient in need thereof
an effective amount of the chemotherapeutic agent, and
an effective amount of the formulation according to the invention.

The invention also relates to a method for reducing or eliminating the need to decrease the dose, interrupt or discontinue the use of a therapeutic agent, for example of a chemotherapeutic agent, in particular Irinotecan, comprising administering a formulation according to the invention to a patient in need of a therapy by said therapeutic agent.

The formulation according to the invention may be administered before, with or after administration of the therapeutic agent which is intended to be eliminated from the lower parts of the gastroinstestinal tract according to the invention. Preferably, the formulation according to the invention is administered before, or together with the therapeutic agent. For example, the subject takes at the same time an antibiotic (or another therapeutic agent, for example a chemotherapeutic agent like Irinotecan, etc.) and a formulation according to the invention.

Thus, for example, administration of the therapeutic agent and of the formulation according to the invention can be simultaneous or sequential (the formulation according to the invention being administered before or after administration of the therapeutic agent), as a single dose or repeated several times a day, for one day or several days. Administration of the formulation of the present invention can begin before administration of the therapeutic agent, and continued after said administration of the therapeutic agent.

Furthermore, the formulation of the invention can also be administered before or after, preferably before, the onset of the adverse effect to be eliminated. In an illustrative embodiment, the formulation of the invention is administered before the patient is treated with a diarrhea-inducing therapeutic agent like Irinotecan, colchicine, or others. The formulation of the invention can be administered once or at multiple times, for example every four or six hours one or two days prior to, as well as after administration of the therapeutic agent, during one or several days.

In a particularly preferred embodiment, in the context of a treatment of a patient with Irinotecan, the formulation of the invention is administered before the administration of Irinotecan to the patient, for example one or two days before, once or several times a day (for example at each meal), and administration of the formulation is continued on the day of administration of Irinotecan and at least 4 days after administration of Irinotecan, preferably several times a day. Ideally, the treatment is continued between 4 to 10 days, preferably 7 days after administration of Irinotecan to make sure that all remaining residual traces of Irinotecan or its metabolites are eliminated from the intestine of the patient.

The invention also relates to a kit comprising at least a first formulation comprising a therapeutic agent whose presence is unwanted in the lower parts of the intestine, and a formulation containing an adsorbent as described above. The invention further relates to a kit according to the invention, for use in one of the methods described above, comprising the administration of the formulations of the kit to a subject in need thereof. The formulations are administrated sequentially (one before the other) or simultaneously, preferably simultaneously.

The invention further relates to a method for the treatment of a disease state in a subject in need thereof, comprising:
administering to the subject a pharmaceutical agent useful for the treatment of the disease, in particular an antibiotic (or any other pharmaceutical agent having side effects when it reaches the lower part of the intestine, as described above), and
administering to the same subject, either sequentially (before or after administration of the pharmaceutical agent) or simultaneously the formulation according to the invention, for eliminating or reducing the amount of the pharmaceutical agent in the lower part of the intestine (i.e., the late ileum, the caecum or the colon).

Representative, non limiting, examples of pharmaceutical agents that can be used in the treatment of a disease state along with the formulation of the invention include antineoplastic agents, for example topoisomerase I inhibitors such as camptothecin derivatives like Irinotecan or Topotecan, anti-inflammatory compounds or inhibitors of interleukin-1 such as diacerhein, pancrelipase (such as Pancrease, Creon, Zenpep), selective phosphodiesterase-4 inhibitors used for the treatment of Chronic obstructive Pulmonary Disease (COPD) such as roflumilast or cilomilast, and compounds having anti-mitotic activities such as colchicine.

As described above, the content of the formulation according to the invention may be adapted to the absorption profile of most types of therapeutic agents, and in particular to most kind of antibiotic agents. As an effect, the release of the adsorbent is most reliable and consistent to achieve no interaction with the normal therapeutic agent absorption process. Accordingly, and as provided above, the delivery of the adsorbent may be delayed in such a way so as to provide delivery at a predetermined time after the therapeutic agent, for example an antibiotic, is completely absorbed to have its therapeutic effect. This is achieved through specific coatings, providing both protection in the upper part of the intestinal tract and efficient adsorbent delayed-release. This provides a major and very innovative advantage over the above-mentioned general and specific approaches.

The sequence of administration can also be adapted by the person skilled in the art. For example, a pharmaceutical treatment may comprise the administration of the pharmaceutical agent by routes different from the oral route. For example, a pharmaceutical agent can be administered via a parenteral route, such as by an injection (for example intravenous, intra-arterial, intrathecal, intramuscular injection). In this case, the person skilled in the art will adapt the timing of administration of the formulation of the invention according to its knowledge of the timing of excretion of the pharmaceutical agent in the gastrointestinal tract.

The formulation may also be administered to a patient who suffers from the effects of bacterial or fungal toxins on the colon. Examples of such toxins include mycotoxins, endotoxins or enterotoxins, such as those produced by *Clostridium difficile* (believed to be a major cause of post-antibiotic diarrhea throughout the world). In this embodiment, the adsorbents are administered in a therapeutically effective dosage to adsorb the toxins.

The invention thus also relates to a formulation as described above, for use in a method for eliminating the effects of bacterial or fungal toxins in the colon. The invention further relates to a method for eliminating the effects of bacterial or fungal toxins on the colon, comprising administering to a subject in need thereof an effective amount of the formulation of the invention.

Furthermore, the invention also relates to a formulation as described above, for use in a method for the treatment of disease states characterized by the accumulation of substances in the lower part of the gastrointestinal tract, this accumulation being responsible for the development of a number of pathological conditions. For example, the formulation can be useful for the treatment of conditions such as, but not limited to, hepatic encephalopathy, irritable bowel syndrome, chronic renal disease, *C. difficile* associated diarrhea or antibiotic associated diarrhea. Representative substances which can be adsorbed by the formulation disclosed herein include, but are not limited to, ammonia, indoles, advanced glycation end products (AGEs) and certain bacterial toxins.

The formulation of the invention can be administered to a patient who suffers from Chronic Kidney Disease (CKD). Advanced glycation end products (AGEs), phenols (for example p-cresylsulphate) and indoles (for example, indoxyl sulfate) are representative toxins generated or introduced in the body via the intestine which can be involved in CKD. Accordingly, in a particular embodiment, the invention relates to the formulation as defined above for use in a method for the treatment of CKD. The invention more specifically relates to a formulation as described above, for use in a method for eliminating toxins involved in the generation of uremic retention solutes. The invention further relates to a method for eliminating the effects of toxins involved in the generation of uremic retention solutes, comprising administering to a subject in need thereof an effective amount of the formulation of the invention. More specifically, the invention relates to the elimination or reduction of the amount of AGEs, phenols (for example p-cresylsulphate) and/or indoles (for example, indoxyl sulfate) in the lower part of the intestine (i.e., the late ileum, the caecum or the colon).

The formulation of the invention can further be administered to a patient who suffers from Inflammatory Bowel Disease (IBD), in particular from ulcerative colitis or Crohn's disease. Thanks to the formulation of the invention, it is now possible to induce or re-establish immunological tolerance by recomposing the commensal microflora in the intestine by adsorbing excess non specific mucosal bacteria or aggressive metabolites and mediators that accumulate in the intestinal mucosa such as nitric oxide, oxygen radicals, prostaglandins, leukotrienes, histamine, proteases, and matrix metallo-proteinases. The invention thus relates to the formulation as described above, for use in a method for inducing or re-establishing immunological tolerance in a patient who suffers from an IBD, in particular from ulcerative colitis or Crohn's disease. The invention therefore also relates to a method for the treatment of an IBD, in particular of ulcerative colitis or Crohn's disease, comprising administering to a patient in need thereof a formulation according to the invention. The invention further relates to a formulation as described above for use in a method for eliminating or reducing the amount of excess non specific mucosal bacteria or aggressive metabolites and mediators that accumulate in the intestinal mucosa such as nitric oxide, oxygen radicals, prostaglandins, leukotrienes, histamine, proteases or matrix metallo-proteinases.

The formulation according to the invention can also be used to treat Hepatic Encephalopathy (HE). A key role is thought to be played in this disorder by circulating gut-derived toxins of nitrogenous compounds, notably ammonia. The formulation according to invention can for example be used to adsorb ammonia produced by bacteria in the gut of a patient in need thereof. As such, the invention relates to a formulation as described above, for the elimination or reduction of nitrogenous compounds, notably ammonia, in the gut of a subject in need thereof. The invention also relates to a method for eliminating or reducing the amount of nitrogenous compounds, notably ammonia, in the gut of a subject in need thereof, comprising administering to said patient a therapeutically effective amount of a formulation as described above.

When the subject to be treated is an animal, for example pet or farm animal, the formulation according to the invention may be incorporated in food. For example, the formulation according to the invention may be incorporated in a medical food (or drug food) either without or with an antibiotic, if the food is intended to be used as a therapeutic formulation. Alternatively, the formulation according to the invention may be in the form of a premix food, which will serve as a food additive.

Veterinary Applications:

The formulation according to the invention is able to release an adsorbent in a specific part of the intestine of a subject. As mentioned above, the subject may be a pet or farm animal. For example, the subject may be a pig, a dog, a cat, a horse or fowl.

Adsorbents, besides being useful in a therapeutic context, are able to eliminate a wide range of molecules. Accordingly, the formulations according to the invention may be implemented in methods in which the release of an adsorbent in the lower parts of the intestine would be advantageous.

For example, the formulation according to the invention may be used for reducing flatulencies (for example via $H_2S$ adsorption), stool smell (for example via ammonium adsorption), halitosis, food intolerance, etc.

The present invention will be further understood with reference to the following non-limiting examples.

EXAMPLES

Example 1: Kinetics of Levofloxacin Adsorption by Activated Charcoal in Simulated Colonic Fluid A solution of levofloxacin (50 µg/ml) was incubated with non formulated activated charcoal (NFAC) in simulated colonic fluid (50 mM sodium phosphate buffer pH 6.0, 100 mM NaCl) with gentle mixing at 37° C. The ratio of NFAC to levofloxacin was either 3:1 or 10:1.

Samples were withdrawn after 0, 0.5, 1 and 2 h incubation, centrifuged and filtered, and the amount of levofloxacin remaining in the supernatant was measured by its absorbance at 287 nm.

As shown in FIG. 1, even with the lowest ratio of NFAC to levofloxacin, all of the antibiotic was adsorbed onto the charcoal after 30 min incubation.

Example 2: Microbiological Assay of Ciprofloxacin and Levofloxacin

The microbiological assay consists in measuring the biological activity of an antibiotic, i.e. its capacity to inhibit the growth of an indicator bacterial strain. To this end, agar plates were made with Difco medium 5, containing *E. coli* strain CIP 7624 as indicator strain. 20 μl samples containing the antibiotic to be measured were spotted onto paper discs applied directly onto the surface of the agar plates. After 18 h incubation at 37° C., the diameters of the zones around the paper discs where bacterial growth had been inhibited by the presence of the antibiotic were measured.

Figure 2:
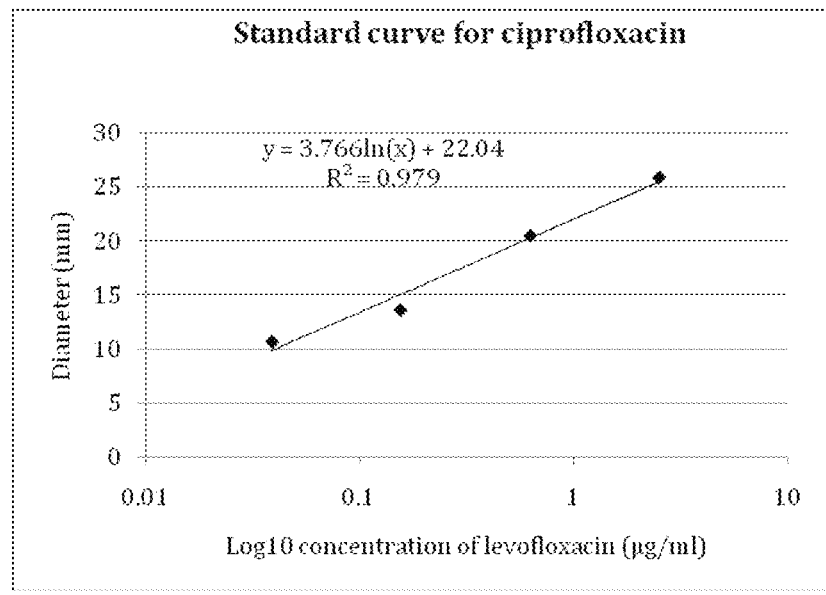
FIG. 2: calibration of the microbiological assay for ciprofloxacin: relationship between Log 10 ciprofloxacin concentration and growth inhibition diameter.

As shown in FIG. 2, there is a linear relationship between the logarithm of the concentration of the antibiotic solution ($\log_{10}$ μg/ml) and the diameter (mm) of growth inhibition. The assay was linear from 0.04 to 5 μg/ml ciprofloxacin.

When 20 μl of a suspension of non formulated charcoal was spotted onto the discs, no growth inhibition was observed, showing that charcoal alone did not have any effect on bacterial growth in this assay.

A similar assay was set up for levofloxacin using the same medium and indicator strain; this assay gave a linear response from 0.15 to 10 μg/ml levofloxacin (not shown).

Figure 3:
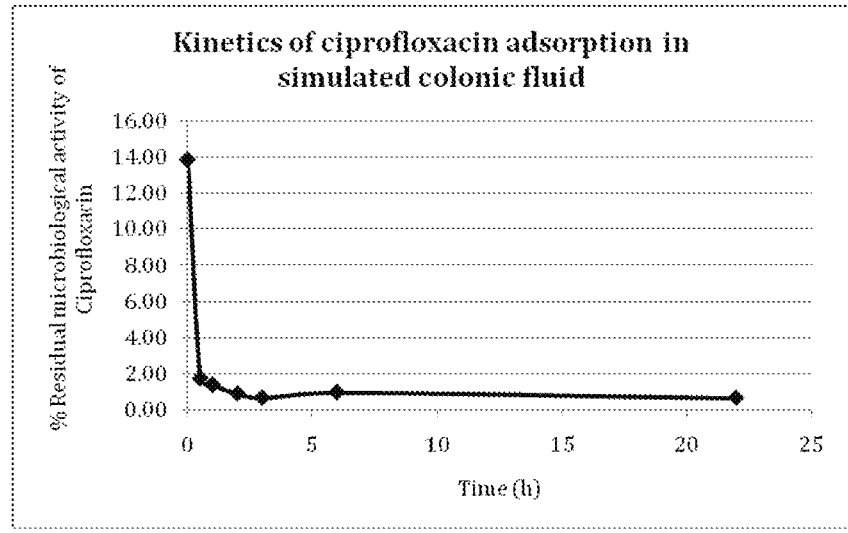
FIG. 3: adsorption of ciprofloxacin on activated charcoal measured by the microbiological assay.

Example 3: Kinetics of Ciprofloxacin Adsorption by Activated Charcoal Measured by Microbiological Assay A solution of ciprofloxacin (50 μg/ml) was incubated with 150 μg/ml activated charcoal in modified simulated colonic fluid (18.7 mM maleic acid, 84 mM NaCl, pH 6.0). Samples were withdrawn at various times, centrifugated, and the amount of ciprofloxacin remaining in the supernatant was measured by a microbiological assay as described in example 2. As shown in FIG. 3, the result was essentially the same as in the experiment described in example 1, where antibiotic concentrations were measured spectrophotometrically. Almost all of the antibiotic was adsorbed onto the charcoal within one hour. It is worthy to note that the sample marked as withdrawn at time zero in fact represented approximately one minute of contact between ciprofloxacin and the charcoal; within this short period of time, the charcoal had already adsorbed close to 70% of the antibiotic.

Example 4: Kinetics of Levofloxacin Adsorption by Activated Charcoal in Caecal Medium In order to mimic the conditions under which activated charcoal would interact with antibiotics in vivo, we measured the adsorption of levofloxacin on activated charcoal in the presence of intestinal medium collected from the caecum of healthy piglets (ex vivo conditions).

Figure 4:
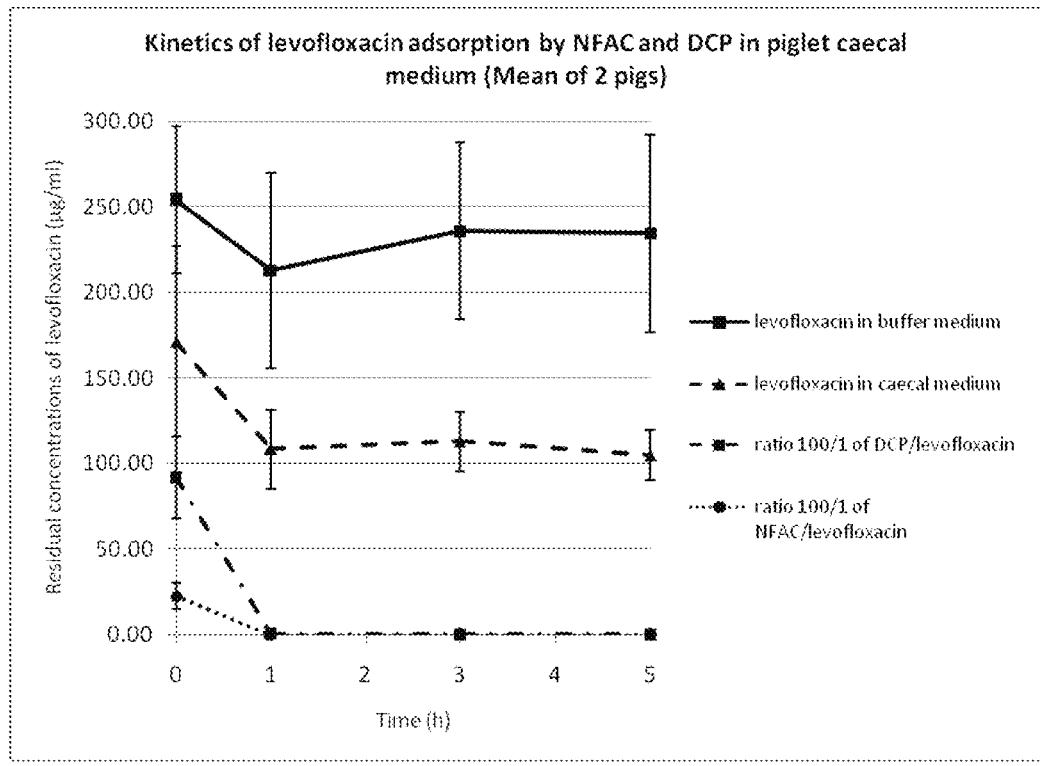
FIG. 4: kinetics of levofloxacin adsorption by NFAC and DCP (deformulated coated pellets) in piglet caecal medium.

Levofloxacin (800 μg/ml) was preincubated with an equal volume of piglet caecal medium for 2 h at 37° C. with gentle agitation. Similarly, a suspension of non formulated activated charcoal, or deformulated product (deformulated coated pellets, or DCP) containing 80 mg/ml of equivalent activated charcoal was incubated under the same conditions as above with an equal volume of piglet caecal medium. Deformulation is carried out as provided in Example 6 below. The antibiotic and charcoal suspensions in caecal medium were then mixed in equal volumes, and incubated for up to 5 h at 37° C. under gentle agitation; this represented a 100:1 ratio of charcoal to levofloxacin. At the indicated times, samples were withdrawn, centrifuged, and the amount of free and active antibiotic remaining in the supernatant was measured by the microbiological assay described above. FIG. 4 shows that approximately half of the antibiotic was adsorbed onto the caecal medium, reaching equilibrium by one hour. In the presence of activated charcoal, no free and active antibiotic remained in the supernatant after one hour, showing that even in the presence of high amounts of actual intestinal medium, activated charcoal was able to efficiently adsorb levofloxacin. The experiment further shows that formulation of the activated charcoal did not affect its capacity to adsorb levofloxacin under such ex vivo conditions.

The experiment was performed with caecal medium extracted from two different piglets; the mean±SD for triplicate determinations is shown.

Example 5: Desorption of Levofloxacin in Different Conditions

Levofloxacin (200 μg/ml final concentration) was adsorbed onto non formulated activated charcoal (NFAC) or deformulated coated pellets (DCP) in the presence of piglet caecal medium as described in example 4, except that the ratio of activated charcoal to levofloxacin was 50:1 in these experiments. After 2 h incubation of Levofloxacin with the ceacal medium and charcoal, the medium was centrifuged, the pellet containing charcoal and caecal medium particles was washed 3 times, and finally incubated for up to 30 days in 50 mM sodium phosphate buffer, containing 100 mM NaCl, at pH 4.0, 7.0 or 10.0 with gentle agitation at 22° C. A control was performed with caecal medium, but in the absence of charcoal; the dissociation experiments were performed in the same volume as the original incubation. At indicated times, a sample was withdrawn, centrifuged, and the amount of free and active antibiotic released in the medium was measured from the supernatant by a microbiological assay.

Figure 5:
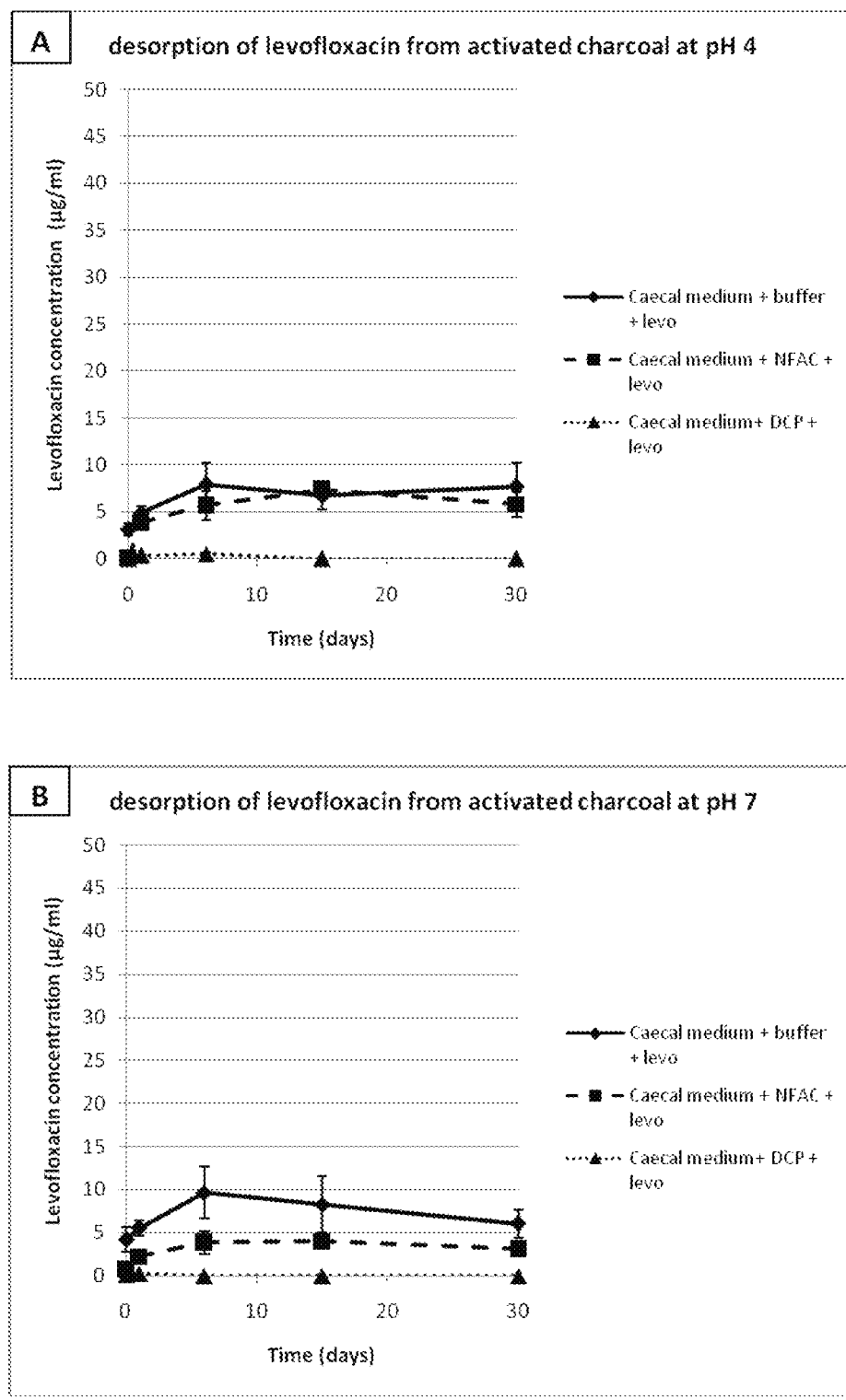
FIG. 5: desorption of levofloxacin from activated charcoal at various pHs. Desorption experiments were respectively performed at pH 4.0 (A), 7.0 (B) and 10.0 (C). The mean of triplicate determinations±SD is shown for each data point.
Figure 5:
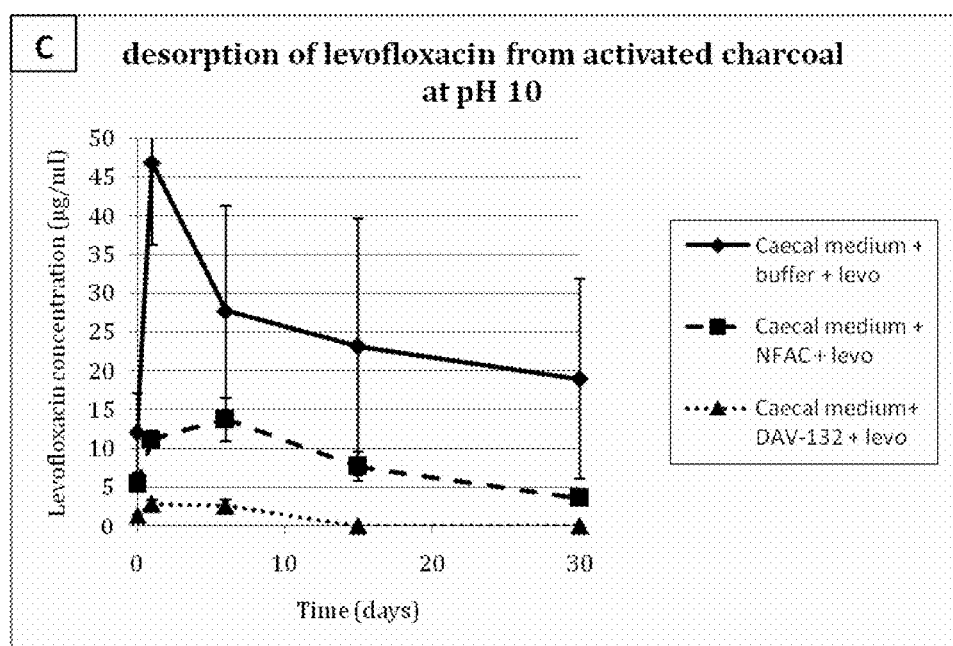

FIG. 5 shows that some antibiotic was released from material in the caecal medium over time, and that this amount was much more important at pH 10.0 than at pH 4.0 and 7.0. A lower amount of levofloxacin was released in the presence of NFAC. Quite remarkably, at pH 4.0 and 7.0, the amount of released of charcoal in the presence of DCP was below the detection limit (0.15 μg/ml levofloxacin). At pH 10.0, the release of levofloxacin was measurable, but did not exceed 2 μg/ml, representing 1% of the original amount of antibiotic in the experiment. Hence, at pH values likely to be encountered in natural media, levofloxacin dissociation from activated charcoal contained in DCP could not be measured.

Example 1: Adsorption Efficacy of Other Antibiotics onto Activated Charcoal

The assay conditions were as follows:

experiments were performed in phosphate buffer saline (PBS) at pH 6 adjusted to colon osmolarity, an initial amount of antibiotic of 200 μg/ml was tested (or less according to maximum solubility of the drug), ratios of activated charcoal/antibiotic of 3/1 and 10/1 were tested, incubation for 2 h at 37° C. (15 ml polypropylene tube, slow rotation 20 rpm), sampling at 0.5 h, 1 h and 2 h, Residual antibiotic dosage (i.e., not adsorbed) was determined by UV/visible spectrophotometric analysis.

Results are shown in tables 1 and 2.

TABLE 1

| Antibiotic tested | Initial amount of ATB (μg/ml) | Residual antibiotic after 30 min | Residual antibiotic after 2 h (*) | Residual antibiotic after 30 min | Residual antibiotic after 2 h (*) |
|---|---|---|---|---|---|
| Ratio of activated charcoal/ATB | | 3/1 | 6/1 after 1 h and 9/1 after 2 h | 10/1 | 20/1 after 1 h and 30/1 after 2 h |
| Beta-lactams | | | | | |
| Amoxicillin | 200 | 19% | | 5% | |
| Ampicillin | 200 | 15% | | <1% | |
| Piperacillin | 200 | <1% | | <1% | |
| Cephalexine | 50 | 26% | | <10% | |
| Cefuroxime | 50 | 5% | | <5% | |
| Ceftriaxone | 200 | 1% | | <1% | |
| Cefotaxime | 200 | <1% | | <1% | |
| Ceftiofur | 50 | <5% | | <5% | |
| Cefixime | 50 | 10% | | <2.5% | |
| Cefdinir | 50 | 9% | | <1% | |
| Cefpodoxime | 50 | 13% | | <3% | |
| Cefquinome | 50 | <5% | | <5% | |
| Cefepime | 50 | 9% | | <5% | |
| Imipeneme | 200 | 6% | | <2.5% | |
| Ertapeneme | 50 | 20% | | <5% | |
| Clavulanate | 50 | 73% | 22% | 39% | 3.5% |
| Tazobactam | 50 | 36% | <20% | <20% | |
| Tetracyclines | | | | | |
| Chlortetracycline | 50 | <3% | | <3% | |
| Oxytetracycline | 200 | <2.5% | | <2.5% | |
| Tetracycline | 200 | <0.1% | | <0.1% | |
| Doxycycline | 200 | <0.1% | | <0.1% | |
| Minocycline | 200 | <0.3% | | <0.3% | |
| Macrolides | | | | | |
| Tylosine | 200 | 66% | <3% | 6% | <3% |
| Erythromycin | 200 | 49% | | <0.3% | |
| Azithromycin | 20 | 78% | | 1% | |
| Clarithromycin | 200 | 54% | | <0.3% | |
| Fluoroquinolones | | | | | |
| Ciprofloxacine | 50 | 2% | | | |
| Levofloxacine | 50 | 1% | | <1% | |
| Marbofloxacine | 200 | <1.25% | | <1.25% | |
| Sulfamides | | | | | |
| Sulfamethoxazole | 50 | 5% | | <5% | |
| Trimetoprime | 50 | 11% | | <3% | |
| Linezolide | 200 | <1.25% | | <1.25% | |
| Glycopeptides | | | | | |
| Vancomycin | 200 | 81% | 27% | 53% | <1.25% |
| Others | | | | | |
| Florfenicol | 200 | 8% | | <2.5% | |
| Tiamulin | 200 | 77.66% | | 71.66% | |
| Tigecycline | 200 | 37% | 21% | <2.5% | |

(*) If antibiotic is not fully adsorbed after 30 min at 3/1 or 10/1 ratio, then extra charcoal is added after 1 and 2 hours
ATB is an abbreviation for antibiotic

TABLE 2 ex vivo adsorption of various antibiotics usually administered to humans

| Antibiotic tested | Initial amount of antibiotic added (µg/ml) | % of residual antibiotic after 5 h | % of residual antibiotic after 5 h | Amount of ATB found in human feces (literature) mean ± SD (µg/g) | range (µg/g) | Dose administered and route of administration | Reference |
|---|---|---|---|---|---|---|---|
| Ratio of activated charcoal/ATB | | 10/1 | 50/1 | | | | |
| Beta-lactams | | | | | | | |
| Amoxicillin | | | | ND | | 500 mg × 3 oral | Internal data |
| Piperacillin | | | | | 0-276 | 4 g i.v. | (1) |
| Cefuroxime | | | | ND | | 250 mg × 2 oral | Internal data |
| Ceftriaxone | | | | 152 ± 53 | 0-657 | 2 g × 1 i.v. | (2) |
| Cefdinir | 200 | 0.2% | 0.15% | | | | |
| Cefpodoxime | 200 | 2% | 5% | 550 ± 460 | 95-550 | 200 mg × 2 oral | Internal data |
| Imipeneme | | | | 0.7-11.3 | | 500 mg × 4 i.v. | (3) |
| Ertapeneme | | | | 37.2 ± 110 | 0-330 | 1 g × 1 i.v. | (3) |
| Clavulanate | | | | | | | |
| Tazobactam | | | | | 0.8-22.2 | 4 g i.v. | (4) |
| Tetracyclines | | | | | | | |
| Tetracycline | 200 | 2.8% | 0% | | | | |
| Macrolides | | | | | | | |
| Erythromycin | 200 | 12% | 0.3% | 978 ± 219 | | 1 g × 2 oral | (5) |
| Azithromycin | | | | 196 | 17-510 | | |
| Clarithromycin | | | | 127.8 ± 58 | | 500 mg × 2 oral | (5) |
| Fluoroquinolones | | | | | | | |
| Ciprofloxacine | 50 | 18% | 0.2% | | | | |
| Levofloxacine | 50 | 8% | | 87.4 ± 59.5 | | 500 mg × 1 oral | (6) |
| Oxazolidones | | | | | | | |
| Linezolide | 200 | 13% | 6.5% | | | | |

ND = Not detectable
(1) Nord, C. E., et al. "Effect of piperacillin/tazobactam treatment on human bowel microflora." J. Antimicrob. Chemother. 31 Suppl A (1993): 61-65.
(2) Pletz, M. W., et al. "Ertapenem pharmacokinetics and impact on intestinal microflora, in comparison to those of ceftriaxone, after multiple dosing in male and female volunteers." Antimicrob. AgentsChemother. 48.10 (2004): 3765-72. (Pletz et al. 3765-72)
(3) Kager, L., et al. "Effect of imipenem treatment versus imipenem surgical prophylaxis on the intestinal microflora." Int. J. Clin. Pharmacol. Res. 8.6 (1988): 441-47.
(4) Brismar, B., C. Edlund, and C. E. Nord. "Comparative effects of clarithromycin and erythromycin on the normal intestinal microflora." Scand. J. Infect. Dis. 23.5 (1991): 635-42. (Brismar, Edlund, and Nord 635-42)
(5) Edlund, C., et al. "Comparative effects of moxifloxacin and clarithromycin on the normal intestinal microflora." Scand. J. Infect. Dis. 32.1 (2000): 81-85. (Edlund et al. 81-85)
(6) Edlund, C., S. Sjostedt, and C. E. Nord. "Comparative effects of levofloxacin and ofloxacin on the normal oral and intestinal microflora." Scand. J. Infect. Dis. 29.4 (1997): 383-86. (Edlund, Sjostedt, and Nord 383-86)

As shown in the tables above, most of the antibiotics tested can be adsorbed significantly onto activated charcoal, at a ratio that can be extrapolated in human as clinically relevant. In vitro data correlate well with ex vivo data and where data is available from literature, it can be seen that the amount of residual antibiotic found into the feces can be easily removed with activated charcoal formulation.

Example 7: Pharmaceutical Formulation

The feasibility of an oral dosage form for the site specific delivery of activated charcoal was investigated by testing different pharmaceutical formulation processes. The objective was to develop a galenic form appropriate to the delayed release of activated charcoal in the later part of the gastrointestinal tract yet preserving as much as possible the adsorption characteristics of the charcoal.

Activated charcoal is a very challenging product to formulate because of its physicochemical properties such as low density, hydrophobicity, wetting properties, etc. Attempting to formulate the charcoal for the intended use described in this invention at a therapeutic dose for human administration was not possible using conventional direct compression because of the very low cohesive properties of activated charcoal. Even simple wet granulation and compression lead to tablets exhibiting poor adsorption properties. The inventors, however, managed to formulate activated charcoal in large amounts in delivery systems that elicit very good stability and disintegration properties: a fast and efficient dispersion of activated charcoal in solution is obtained. Furthermore, the adsorption properties of activated charcoal are preserved in the described formulation.

Table below shows one example of pellets obtained by wet granulation followed by extrusion spheronization.

TABLE 3 example of a charcoal pellet formulation obtained by wet granulation with carrageenan.

| Formulation | Amount (%) |
| --- | --- |
| Activated charcoal | 85 |
| Gelcarin GP911 (κ-carrageenan) | 15 |
| Water | Sufficient amount for |
|  | 100% |

These pellets constitute the core of the formulations used throughout the present examples.

These pellets are then further coated with specific pH-dependent polymer coating, such as Eudragit® FS30D or Eudragit® L30D55 (Evonik, Darmstadt, Germany) for example.

The capacity of formulated and non formulated activated charcoal to adsorb various antibiotics in simulated colonic conditions was studied in adsorption kinetic studies.

For this purpose, coated pellets of activated charcoal were first deformulated in a buffer (50 mM sodium phosphate buffer, 80 mM NaCl, pH 7.5) for at least 30 minutes at 37° C. Suspensions of non formulated activated charcoal (NFAC) were also prepared in this buffer. Then, the adsorption capacity of a suspension of deformulated pellets (formulation) and a suspension of NFAC were tested with a levofloxacin solution (levo).

Figure 6:
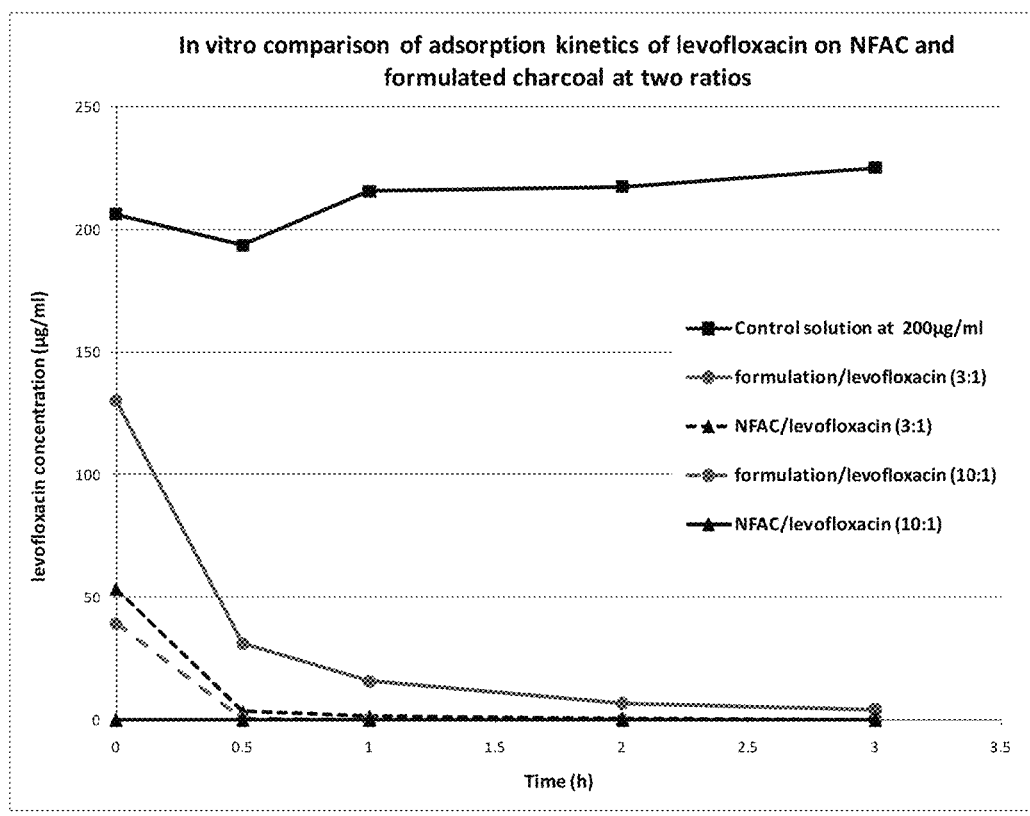
FIG. 6: In vitro comparison of adsorption kinetics of levofloxacin on NFAC and formulated charcoal at two charcoal/levofloxacin ratios.

FIG. 6 presents, as an example, a comparison of several adsorption kinetics of levofloxacin on NFAC and deformulated pellets. The experiments were performed as in the previous example, with pellets coated with 20% Eudragit FS30D.

Two studied ratios of NFAC to levofloxacin and deformulated pellets to levofloxacin are presented, 3:1 and 10:1. A control sample, made of the solution of levofloxacin, was also analyzed during the adsorption kinetic.

Full adsorption of levofloxacin on deformulated pellets and NFAC is observed after 60 minutes for the 10:1 ratio. The adsorption is almost complete for the ratio 3:1 on the formulation and complete on NFAC. Hence, the adsorption properties of the activated charcoal are essentially maintained through the formulation processes.

Limited influence of time, temperature and humidity could be observed in bulk storage conditions of the formulation. Excellent stability was obtained at room temperature after 9 months in bulk storage conditions as determined by measurement of disintegration time and ciprofloxacin adsorption after one hour.

More precisely, stored pellets were disintegrated in the simulated colonic medium (50 mM sodium phosphate buffer, 80 mM NaCl, pH 7.5) and spiked with a known amount of ciprofloxacin. The kinetics of disintegration of the pellets was monitored. As pellets disintegrate and release the activated charcoal, the ciprofloxacin concentration of the solution decreases. The results presented in Table 4 below represent the remaining percentage of ciprofloxacin in the media at different sampling times. These results prove that the disintegration properties of the pellets are maintained during 9 months in bulk storage conditions.

TABLE 4

Bulk stability of FS30D-coated charcoal formulation stored at room temperature in glass vials. Charcoal formulation/ciprofloxacin ratio was 9:1. Results are expressed as the percentage of free ciprofloxacin remaining in the solution.

| Time (min) | T0 | T6 months | T9 months |
| --- | --- | --- | --- |
| 0 | 95 | 99 | 100 |
| 30 | 49 | 51 | 85 |
| 60 | 2 | 4 | 7 |
| 120 | <1 | 2 | 2 |
| 180 | <1 | <1 | <1 |

Example 8: In Vitro Release Profile of Activated Charcoal and Adsorption Kinetics of Ciprofloxacin One of the major issues with charcoal formulation is the disintegration profile of the charcoal pellet into the medium to allow maximum adsorption efficiency. The formulation described earlier has been tested in a BioDis dissolution tester (USP III release apparatus) using several simulated intestinal media spiked with ciprofloxacin at a concentration of 50 μg/mL. In this experiment, approx. 73 mg of coated pellets were submitted to dissolution in the BioDis system, by being successively incubated for the indicated times in media whose composition reflect the pH, buffer capacity and osmolarity of the various gastro-intestinal compartments. Samples of each medium were withdrawn and analyzed to determine the remaining ciprofloxacin concentration. Ciprofloxacin was only adsorbed by the active charcoal released from the formulation, hence ciprofloxacin adsorption was taken as a proxy or active charcoal release from the formulation.

The simulated gastro-intestinal media are described below:

Simulated gastric medium: 34.2 mM NaCl, pH adjusted to 1.6 with HCl.

Simulated duodenum and proximal jejunum medium: 19.1 mM maleic acid, 70 mM NaCl, 31.6 mM NaOH, pH=6.5

Simulated middle and late jejunum medium: 25 mM HEPES, 121.6 mM NaCl, pH adjusted to 7.0

Simulated ileal medium: 18 mM HEPES, 132.1 mM NaCl, pH adjusted to 7.5

Simulated colonic medium: 18.7 mM maleic acid, 83.7 mM NaCl, 25.6 mM NaOH, pH adjusted to 6.0

Figure 7:
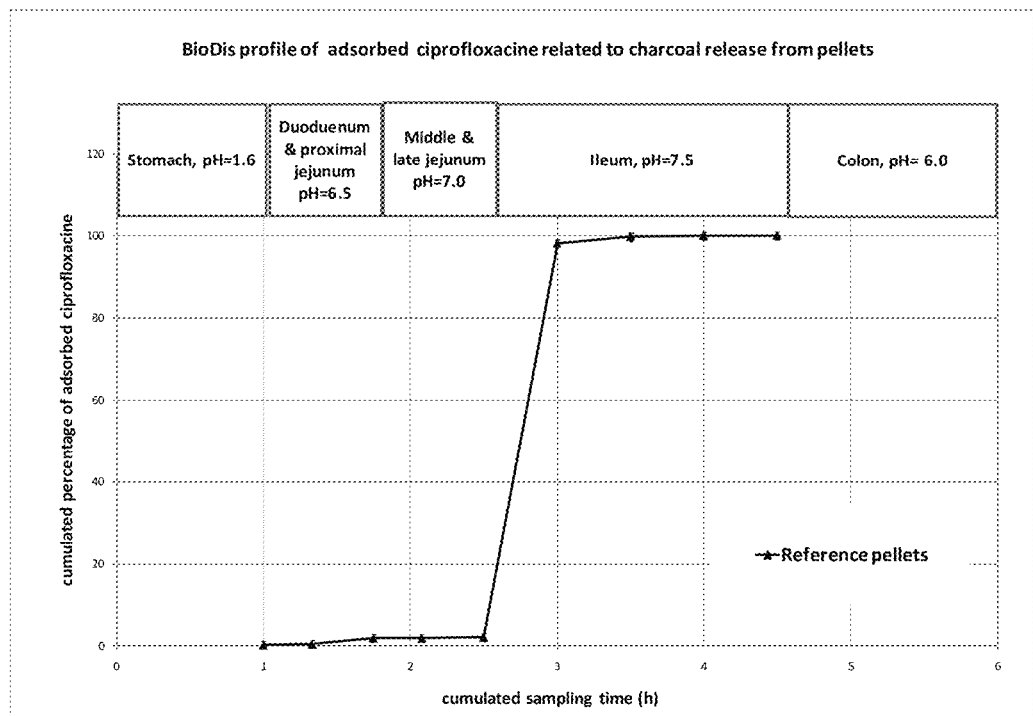
FIG. 7: BioDis profile ciprofloxacin adsorption onto charcoal released from FS30D-coated pellets.

A shown in FIG. 7, the carrageenan-based charcoal formulation coated with FS30D, as a coating example, demonstrated no charcoal release until reaching pH of 7.5. Then, adsorption of ciprofloxacin was very fast and complete within half an hour after charcoal dispersion.

Example 9: Other Possible Formulations

Antibiotics have different absorption profiles in mammals, some being absorbed early and some being absorbed later. The later will reach their maximum plasma concentration after 2 to 4 hours. Formulations can be developed to allow a more delayed adsorbent delivery to avoid any impact on the normal absorption process of the antibiotic.

To achieve such a delayed release, pellet formulations were first coated with a sub-coat that prevented them from disintegrating too fast and delayed the disintegration by 30 minutes to 2 hours, depending on the type of polymer used for the sub-coat.

Various formulations were achieved using multiple coating techniques. Table 5 below presents some examples of coating combinations

TABLE 5

Formulations with various sub-coats and final coating with FS30D

| SubCoat type | SubCoat details (w/w final weight) | Outer Coating type | Outer Coating amount |
|---|---|---|---|
| L30D55/NE30D(2/8)* | 15% | — | — |
| L30D55/NE30D(2/8)* | 25% | — | — |
| L30D55/NE30D(2/8)* | 35% | — | — |
| L30D55/NE30D(2/8)* | 12.75% | FS30D | 15% |
| L30D55/NE30D(2/8)* | 21.25% | FS30D | 15% |
| L30D55/NE30D(2/8)* | 29.75% | FS30D | 15% |
| None | None | Aqoat HF | 15% |
| None | None | Aqoat HF | 20% |
| None | None | Aqoat HF | 25% |
| None | None | Aqoat HF | 30% |
| None | None | Aqoat HF | 35% |
| None | None | Shellac Aquagold | 15% |
| None | None | Shellac Aquagold | 20% |
| None | None | Shellac Aquagold | 25% |
| None | None | Shellac Aquagold | 30% |
| None | None | Shellac Aquagold | 35% |
| None | None | Ethylcellulose | 2% |
| None | None | Ethylcellulose | 4% |
| None | None | FS30D/L30D55 (9/1)* | 15% |
| None | None | FS30D/L30D55 (9/1)* | 20% |
| None | None | FS30D/L30D55 (9/1)* | 25% |
| None | None | FS30D/L30D55 (85/15)* | 15% |
| None | None | FS30D/L30D55 (85/15)* | 20% |
| None | None | FS30D/L30D55 (85/15)* | 25% |
| None | None | FS30D | 15% |
| None | None | FS30D | 35% |

*the numbers in parentheses represent the respective proportions of the indicated Eudragit polymers in the mixture used to prepare the pellet subcoat or outer coat.

Dissolution tests were performed on these pellets in simulated ileal medium, pH7.5 to assess the kinetics of pellet dispersion in such a medium and compare the obtained delays. The ileum medium was spiked with 50 μg/mL ciprofloxacin, and at each sampling time, the amount of residual ciprofloxacin remaining in the solution was quantified; ciprofloxacin adsorption was taken as a proxy for charcoal release.

BioDis tests were also performed on these pellets, as described above, in order to mimic their progression through the gastro intestinal tract. This enabled a more detailed characterization of the delayed release of charcoal from the pellets.

Figure 8:
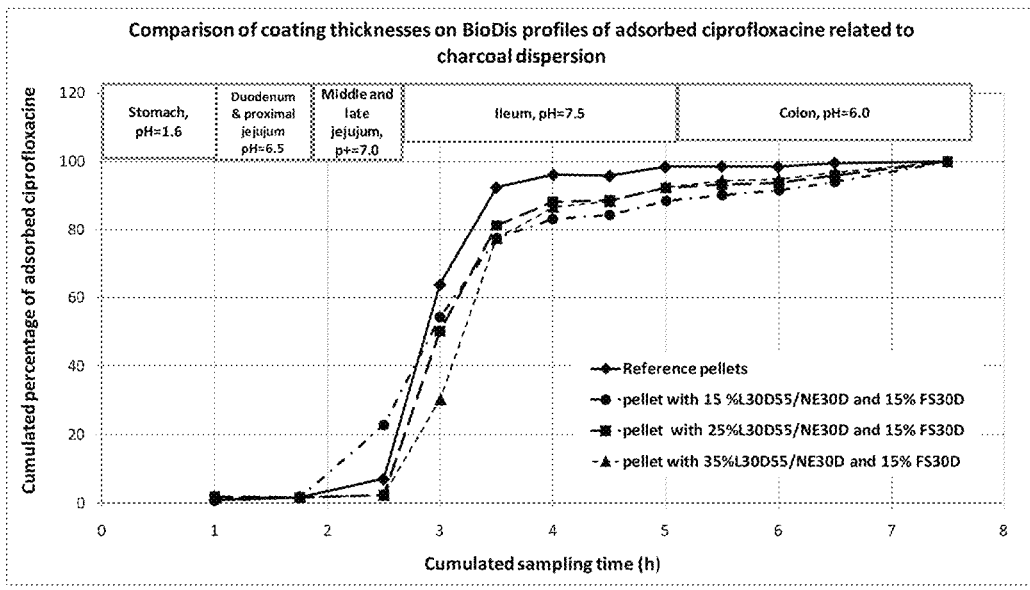
FIG. 8: Comparison of coating thicknesses on BioDis profiles of adsorbed ciprofloxacin onto charcoal released from pellets with a L30D55/NE30D subcoat and a FS30D coating.
Figure 9:
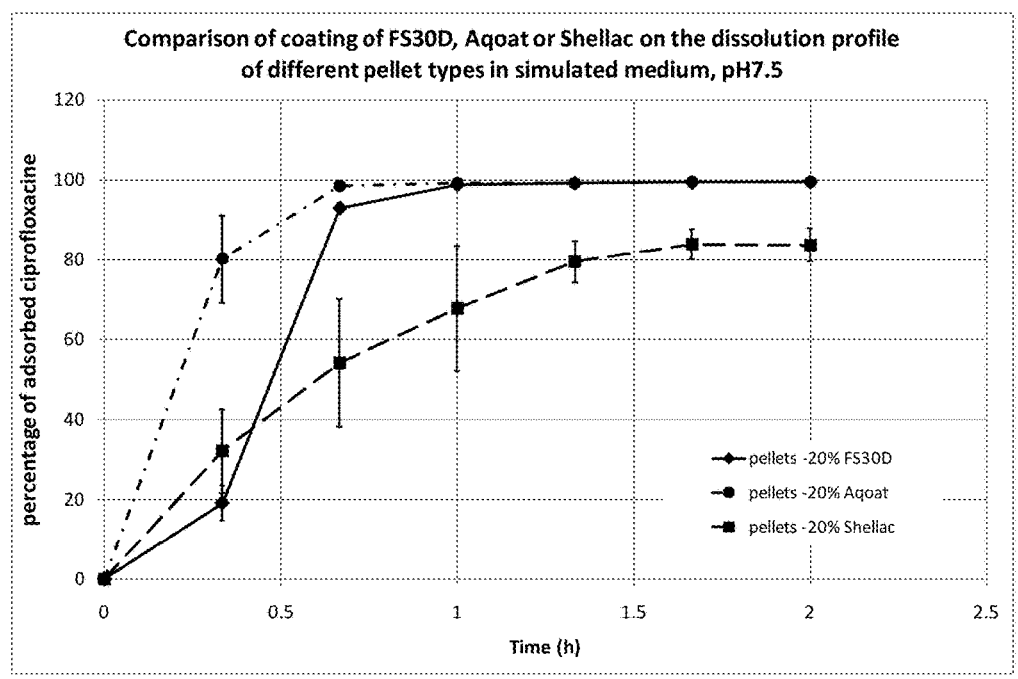
FIG. 9: Comparison of FS30D, Aqoat or Shellac coatings on the dissolution profile of different pellet types in simulated ileal medium, pH7.5 (as measured by ciprofloxacine adsorption).
Figure 10:
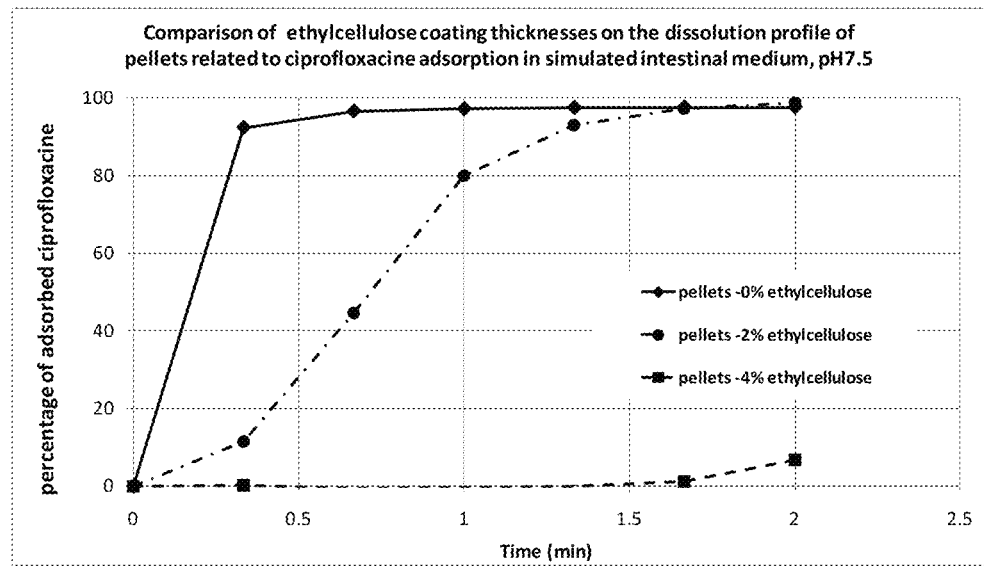
FIG. 10: Comparison of ethylcellulose coating thicknesses on the dissolution profile of pellets in simulated ileal medium, pH7.5 (as measured by ciprofloxacine adsorption).

FIGS. 8-10 describe the charcoal release, measured as ciprofloxacin adsorption, from some of the formulations described in Table 5.

As can be seen in FIG. 8, a first coating (subcoat) made of a mixture L30D55/NE30D polymers representing 35% w/w of the final weight of the pellets, elicited a delayed adsorption of ciprofloxacin, meaning that charcoal exhibited a delayed release of charcoal as compared to the formulation made with an outer FS30D coat by approx. 30 minutes.

As can be seen in FIG. 9, the Aqoat-coated pellets exhibited a dissolution that was approx 30 min faster than those coated with an equivalent amount of FS30D. Ciprofloxacin adsorption was complete within one hour. For pellets coated with Shellac, delayed dissolution was observed for the film and disintegration of the charcoal pellets was prolonged for at least two hours As can be seen in FIG. 10, the effect of various thicknesses of ethylcellulose coatings was assessed on pellet dissolution. An intermediate coat consisting in 2% ethylcellulose induced a significant delayed release of activated charcoal, by approximately 40 minutes to one hour, compared to 20% FS30D coating.

Such formulations might be of interest in providing delayed and prolonged release of the adsorbent.

Figure 11A:
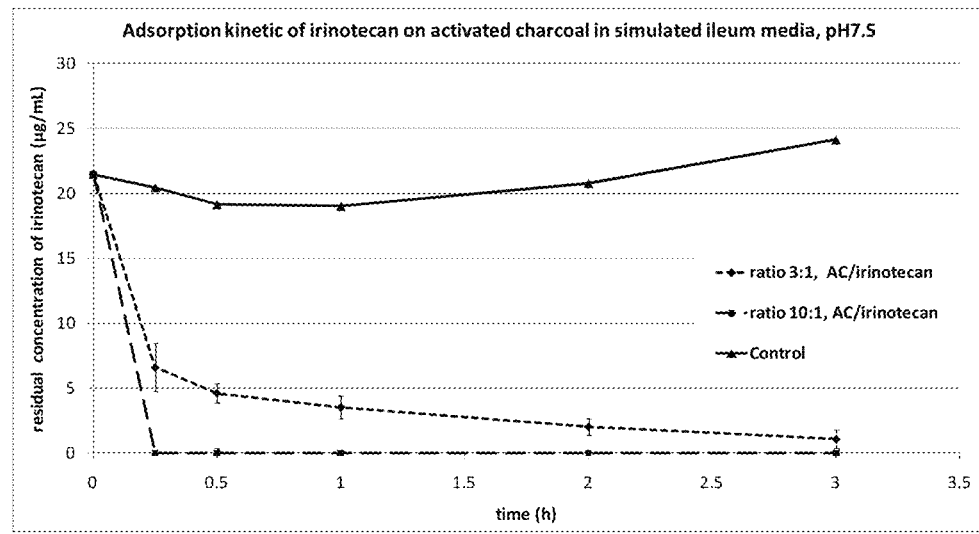
FIG. 11A: Adsorption kinetics of irinotecan on activated charcoal in simulated ileum media, pH7.5.

Example 10: In Vitro Adsorption Kinetics of Irinotecan and SN-38 onto Activated Charcoal The adsorption kinetics of irinotecan and its active metabolite SN-38 onto active charcoal were determined in vitro (FIGS. 11A and 11B respectively).

The capacity of activated charcoal to adsorb irinotecan (200 μg/mL initial concentration) was assessed in simulated ileal medium (18 mM HEPES, 132.1 mM NaCl, adjusted to pH 7.5 with NaOH). The respective proportions of activated charcoal and irinotecan were 3:1 and 10:1, in relation to irinotecan. Samples were centrifuged, filtered, and diluted ten-fold, prior to determination of the non-adsorbed concentration of irinotecan by measuring its absorbance at 368 nm using a spectrophotometer. As can be seen in FIG. 11A, half of the amount of irinotecan was adsorbed in about 12 minutes with a 3:1 ratio of activated charcoal/irinotecan. Complete adsorption was achieved in about 15 minutes with a 10:1 ratio of activated charcoal/irinotecan.

Figure 11B:
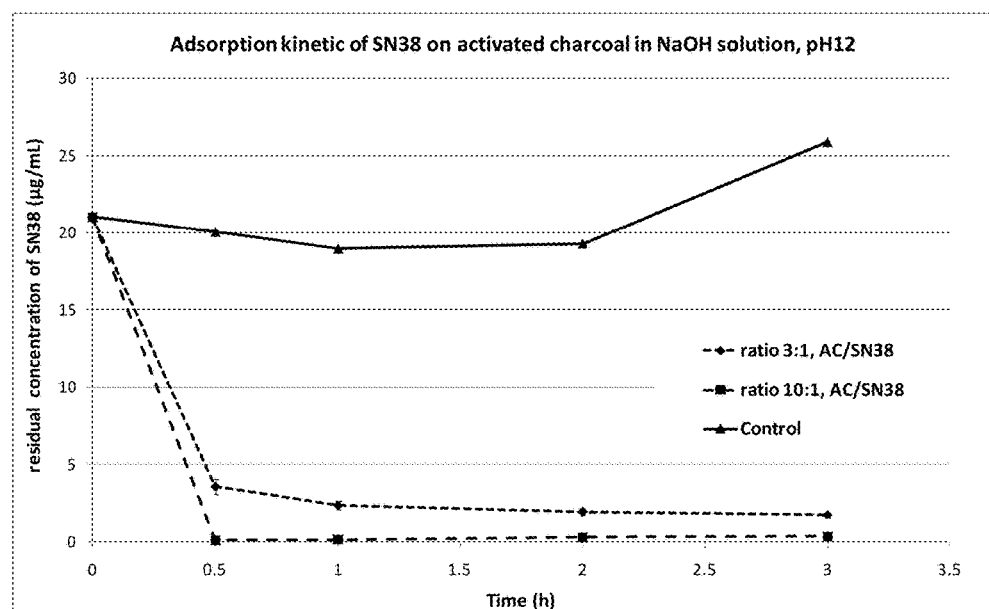
FIG. 11B: Adsorption kinetic of SN38 on activated charcoal in 1 mM NaOH, pH 12.

FIG. 11B shows the capacity of activated charcoal to adsorb SN-38. SN-38 was dissolved at a concentration of 50 μg/mL in 0.01M NaOH pH 12. Non adsorbed SN-38 was detected after centrifugation and filtration by at its absorbance at 411 nm using a spectrophotometer. As can be seen in FIG. 11B, SN38 adsorption was complete in about than 30 minutes with an activated charcoal/SN-38 ratio of 10:1.

Figure 11C:
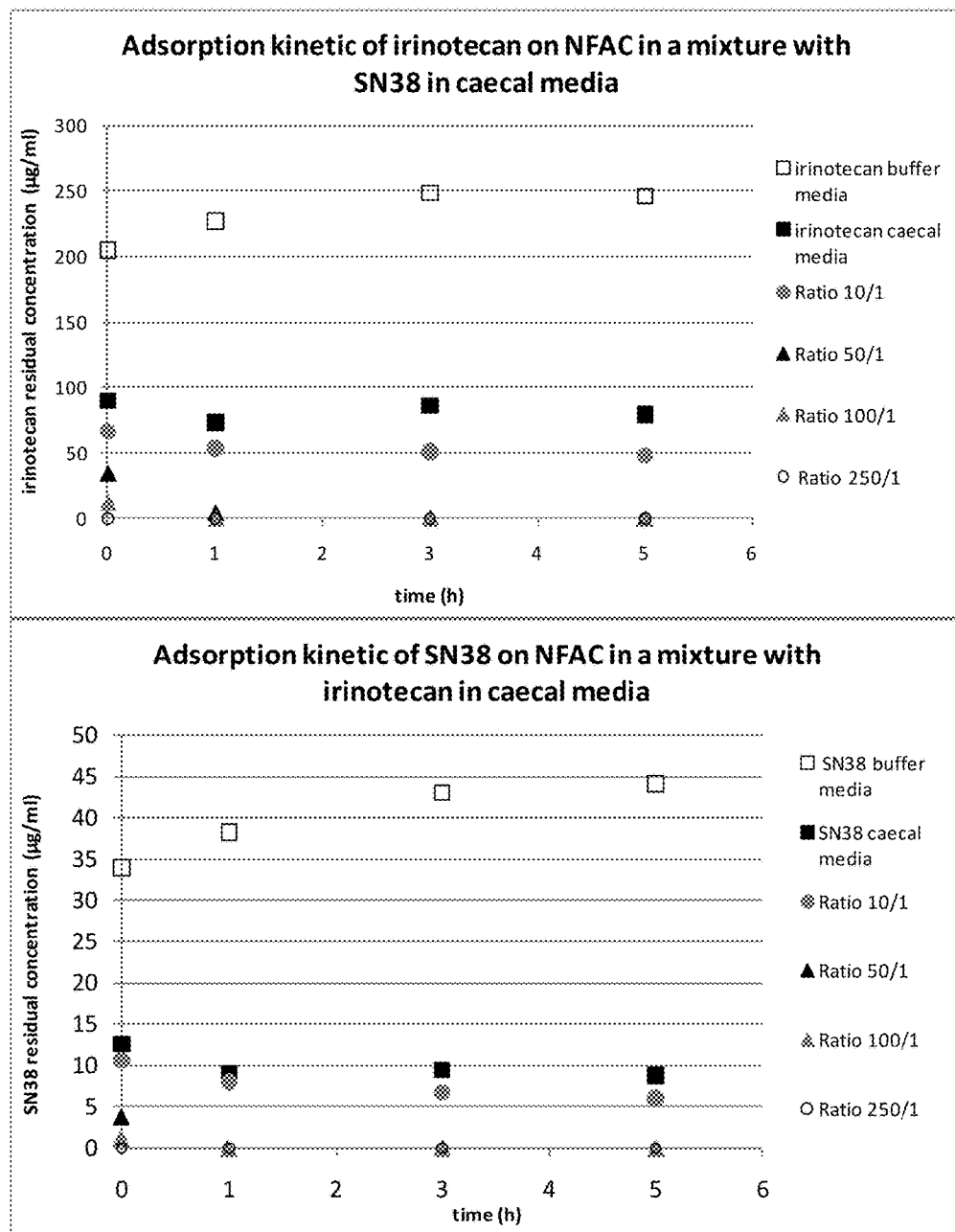
FIG. 11C: Adsorption kinetics of irinotecan on activated charcoal in caecal media of piglet spiked with a mixture of SN38 and irinotecan.
Figure 11D:
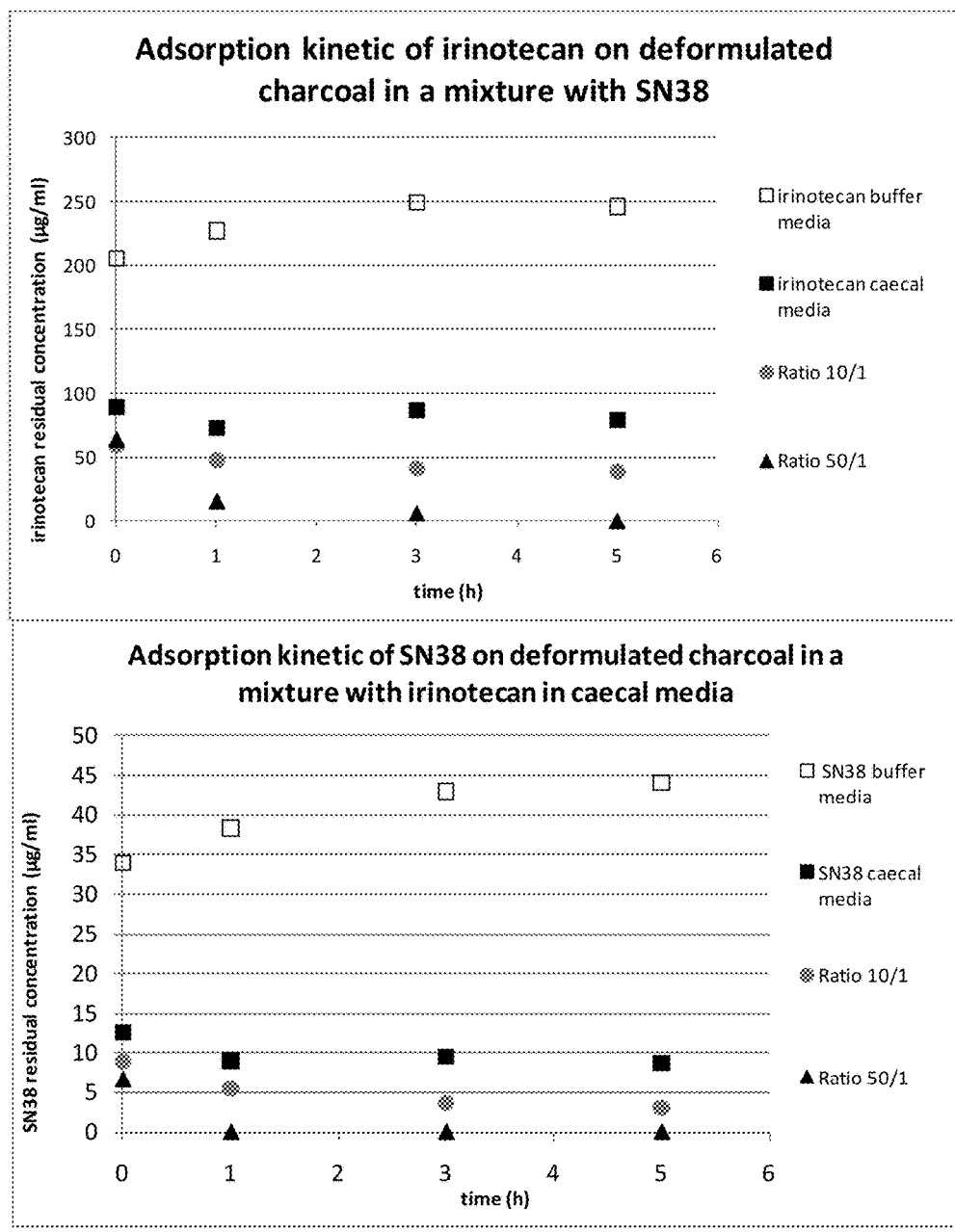
FIG. 11D: Adsorption kinetics of SN38 on deformulated coated pellets in caecal media of piglet spiked with a mixture of SN38 and irinotecan.

The adsorption kinetics of irinotecan and its metabolite SN-38 onto activated charcoal (NFAC) (FIG. 11C) and charcoal released from deformulated coated pellets (DCP) (20% of FS30D coating) (FIG. 11D) were determined ex vivo, in piglet caecal medium.

Piglet caecal medium was spiked with 250 μg/ml irinotecan and 50 μg/ml SN-38, and preincubated for 2 h at 37° C. NFAC or DCP was pre-incubated with piglet caecal medium diluted 1:1 for 2 hours at 37° C. The ratios of NFAC/irinotecan were 10:1, 50:1, and those for NFAC/SN38 were 10:1, 50:1, 100:1 and 250:1; the ratios of active charcoal from DCP to irinotecan and SN38 were 10:1 and 50:1.

After combining these two pre-incubation mixed, incubation was carried out at 37° C. with gentle agitation for the indicated periods of time. Samples were withdrawn, centrifuged, the supernatant was filtered and analysed for the presence of irinotecan and SN38 by HPLC.

Example 11: In Vivo Performance of Targeted-Release Activated Charcoal in Reducing the Emergence of Bacterial Resistance to Antibiotic A proof of concept (POC) study of the ability of targeted-release activated charcoal (coated pellets of activated charcoal) to reduce the emergence of bacterial resistance during antibiotic treatments was performed in piglets, that were weaned 4 weeks after birth, and included into the study two weeks thereafter.

The study was randomized, comparative, open for in-life phase but blinded to treatment for evaluation of microbiological and PK/PD data to demonstrate the efficacy of charcoal delayed-release formulation to:

Decrease antibiotic fecal concentrations

Prevent the emergence of bacterial resistance in gut flora.

Maintain the normal antibiotic absorption process.

To carry out this in vivo POC, the antibiotic to be tested was ciprofloxacin, a fluoroquinolone, administered orally at a dose of 1.5 mg/kg/day. This type of study will be applicable for any antibiotic considered by Da Volterra. The methods used in evaluating the decrease of antibiotic fecal concentrations and the emergence of bacterial resistance were developed by Da Volterra. The experiments were conducted under GLP conditions. Piglets, from the same batch, had not been treated with antibiotics since birth.

Figures 12, 13:
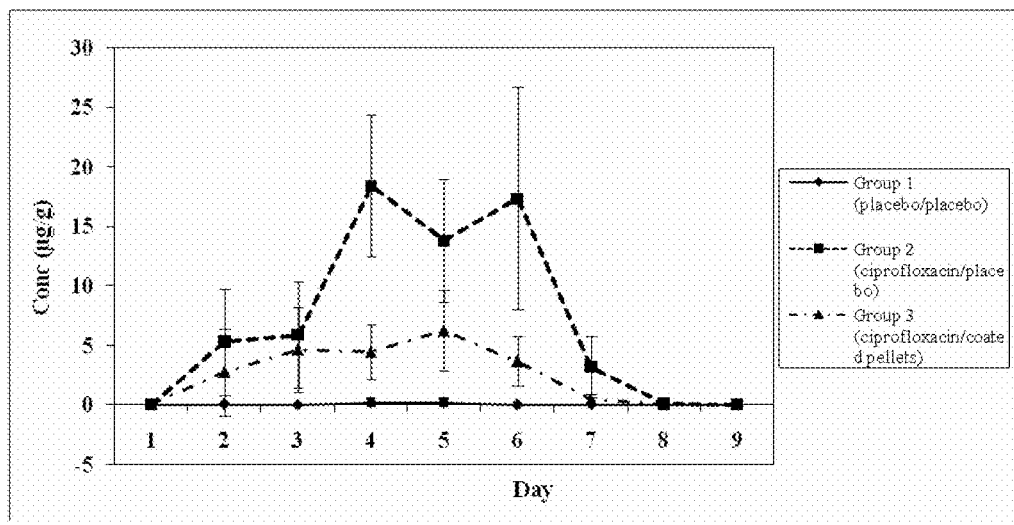
FIG. 12: In vivo performance of targeted-release activated charcoal in reducing the emergence of bacterial resistance to antibiotic—study design.
FIG. 13: Average evolution of faecal ciprofloxacin concentrations by group (n1=6, n2=11, n3=12). In this graph, we represent also for each group the 95% confidence interval defined as [mean−1.96*SEM; mean+1.96*SEM] where SEM is the standard error of the mean.

The study design is depicted in FIG. 12.

The Primary Endpoints of this Study were:

Pharmacokinetic Criteria:

To compare the concentration of ciprofloxacin with or without coated pellets in feces by the comparison of Neperian logarithm of the Area Under the Curve (AUC) of fecal ciprofloxacin concentrations between Day 1 and Day 9 (log $AUC_{D1-D9}$).

The AUC between Day 1 and Day 9 were computed by trapezoidal approach using SAS software and are analyzed with descriptive statistics and compared across groups by t-tests (on log $AUC_{D1-D9}$).

To compare the plasma concentrations of ciprofloxacin with or without coated pellets by comparing Neperian logarithm of Area Under the Curve (AUC) of ciprofloxacin plasma concentrations between 0 h and the time $T_{last}$ corresponding to the last observed value (log AUC) (This choice of $AUC_{0-last}$ can be explained by the very high percentages of extrapolation for $AUC_{0-\infty}$.)

Neperian logarithm of ciprofloxacin plasma maximum concentration (Cmax) (log Cmax)

This was performed by a Non Compartmental Approach (NCA), linear/log trapezoidal method, via WinNonLin software (version 5.2) to compute $C_{max}$ and AUC. Ciprofloxacin plasma concentrations at 0 h were considered to be 0 ng/mL. Log AUC and log $C_{max}$ were then calculated and analyzed with descriptive statistics.

Pharmacodynamics Criterion:

To compare the number of resistant bacteria after treatment by ciprofloxacin with or without coated pellets by comparing the AUC of counts of Enterobacteriaceae resistant to ciprofloxacin, and to nalidixic acid, from Day 1 to Day 6 (treatment) normalized to Day −1/1. The bacterial counts were obtained by performing 100 µl of 1/10 dilution of feces plated on Drigaski agar. The counts of Enterobacteriaceae resistant to ciprofloxacin and nalidixic acid were obtained by plating diluted feces on Drigaski agar with 2 ml/l ciprofloxacin and 20 ml/l nalidixic acid. The detectable limit of resistant Enterobacteriaceae counts was $1.00 \times 10^2$ CFU/g. The baseline was calculated on the mean content of resistant bacteria before treatment and area under the curve is the area between the baseline and the curve of log 10 of ciprofloxacin resistant Enterobacteriaceae counts.

Results

Coated pellets associated to ciprofloxacin was able to decrease the residual fecal concentrations of ciprofloxacin in piglets. The decrease was statistically significant. The comparative results of ciprofloxacin concentration in feces are showed in FIG. 13 and there are summarized in Table 6.

TABLE 6

Fecal ciprofloxacin concentrations: descriptive statistics on individual log AUC D1-D9 by group (n1 = 6, n2 = 11, n3 = 12)
Analysis Variable: log $AUC_{D1-D9}$

| Group | N | Mean | Median | SD | Minimum | Maximum |
|---|---|---|---|---|---|---|
| Group 1 (placebo/placebo) | 6 | −0.24 | 0.00 | 0.59 | −1.37 | 0.28 |
| Group 2 (ciprofloxacin/placebo) | 11 | 4.04 | 4.31 | 0.53 | 3.21 | 4.64 |
| Group 3 (ciprofloxacin/coated pellets) | 12 | 2.98 | 3.21 | 0.53 | 2.03 | 3.62 |

The difference of log $AUC_D$1-D9 between Group 2 (ciprofloxacin/placebo) vs. Group 3 (ciprofloxacin/coated pellets) was statistically significant by comparison t-test (p-value<0.0001).

There were also significant differences between Group 1 (placebo/placebo) vs. Group 2 (ciprofloxacin/placebo) (p-value<0.0001) and between Group 1 (placebo/placebo) vs. Group 3 (ciprofloxacin/Dav-132) (p-value<0.0001).

Figure 14:
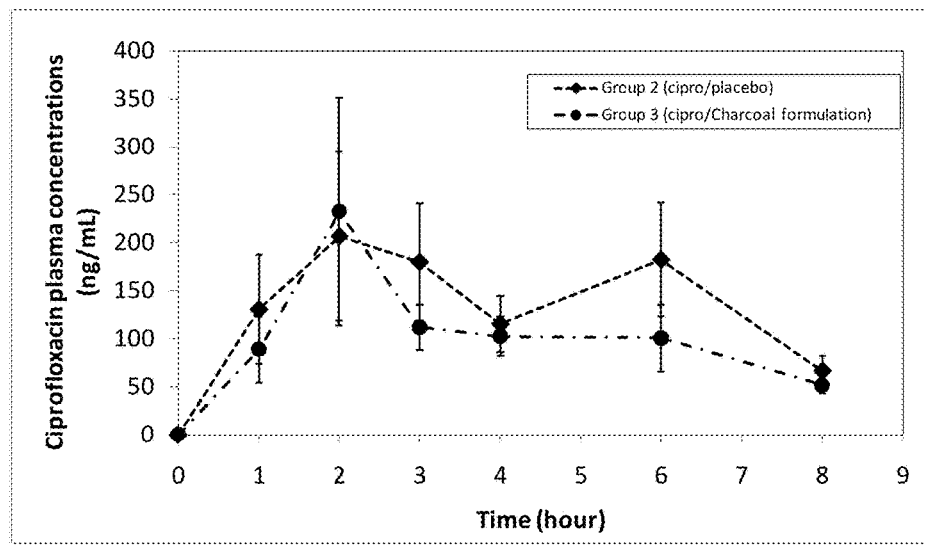
FIG. 14: Average evolution of plasma ciprofloxacin concentrations (ng/mL) by group (n2=n3=12). In this graph, we represent also for each group the 95% confidence interval defined as [mean−1.96*SEM; mean+1.96*SEM] where SEM is the standard error of the mean.

Coated pellets administration associated to ciprofloxacin administration did not result in a significant change in ciprofloxacin plasma concentration. The results on ciprofloxacin concentration in plasma are showed in FIG. 14 and they are summarized in Table 7.

TABLE 7

Plasma concentrations of ciprofloxacin: descriptive statistics on individual log AUC and log Cmax by group (n2 = n3 = 12)

| Group | N | Mean | Median | SD | Min | Max |
|---|---|---|---|---|---|---|
| Analysis Variable: log AUC | | | | | | |
| Group 2 (ciprofloxacin/placebo) | 12 | 6.82 | 6.79 | 0.61 | 5.68 | 7.88 |
| Group 3 (ciprofloxacin/coated pellets) | 12 | 6.54 | 6.46 | 0.62 | 5.50 | 7.52 |
| Analysis Variable: log Cmax | | | | | | |
| Group 2 (ciprofloxacin/placebo) | 12 | 5.48 | 5.44 | 0.71 | 4.18 | 6.64 |
| Group 3 (ciprofloxacin/coated pellets) | 12 | 5.27 | 5.13 | 0.83 | 4.12 | 6.93 |

Figure 15:
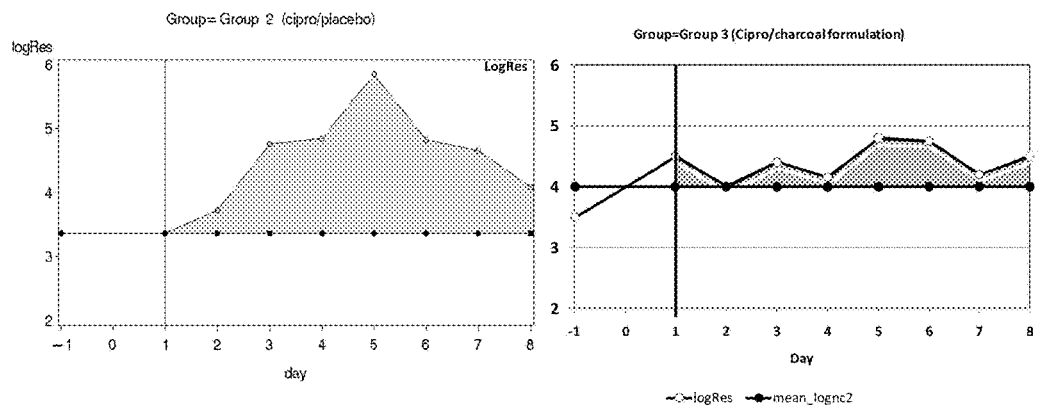
FIG. 15: Resistant bacterial counts: mean of corrected individual AUCciprop1-D8 by treatment group represented by the shaded area between the mean curve of log 10 of ciprofloxacin resistant bacterial counts corrected from the baseline, and the X=0 axis from Day 1 to Day 8 (n1=6, n2=11, n3=12)

The results show that there is no significant difference between these 2 groups on log AUC (t-test p-value=0.28) and on log Cmax (t-test p-value=0.51). Administration of coated pellets together with ciprofloxacin resulted in a decrease in bacterial resistance due to the residual concentration of ciprofloxacin in feces (see FIG. 15).

Ciprofloxacin-resistant Enterobacteriaceae counts in faeces increase significantly with the treatment of piglets with ciprofloxacin. Charcoal formulations according to the invention administered with ciprofloxacin reduced the emergence of bacterial resistance significantly as showed in Table 8. The control group (placebo/placebo) showed no emergence of resistance.

TABLE 8

Resistant bacterial counts: descriptive statistics of individual AUG between Day 1 and Day 6 for ciprofloxacin and nalidixic acid

| Criteria | T-tests Group ciprofloxacin/coated pellets vs. ciprofloxacin/placebo |
|---|---|
| $AUC_{cipro\ D1-D6}$ | 0.0430 |
| $AUC_{nal\ D1-D6}$ | 0.0478 |

Conclusions

The results showed that the formulations according to the invention were:
Well tolerated by piglets
Able to reduce significantly the concentration of ciprofloxacin in the faeces after administration for a five day period together with oral ciproflixacin
Able to significantly reduce the emergence of bacterial resistance to antibiotic treatment
Able to show no interference with the normal process of ciprofloxacin absorption

Figure 16:
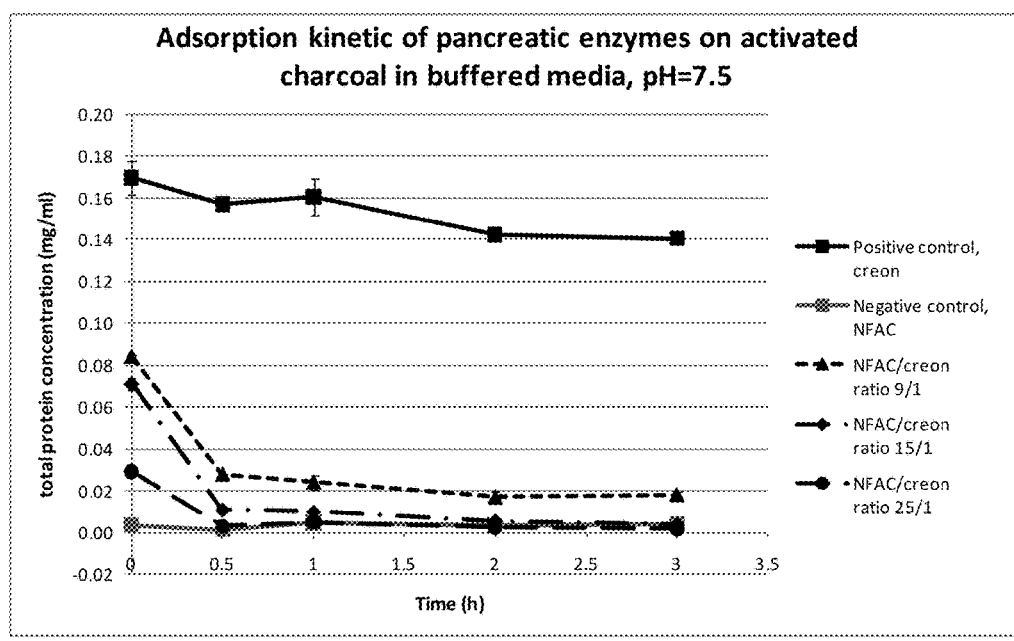
FIG. 16: Adsorption kinetics of Creon on activated charcoal in buffered media, pH7.5.

Example 12: In Vitro Adsorption Kinetics of Pancreatic Enzymes onto Activated Charcoal The adsorption kinetics of Creon, a medicine containing pancreatic enzymes, onto active charcoal were determined in vitro (FIG. 16). The extent of enzyme adsorption onto activated charcoal was assessed using a protein quantification assay (Bradford method). The capacity of activated charcoal to adsorb pancreatic enzymes (1 mg/mL of Creon) was assessed in buffer (50 mM sodium phosphate buffer, 80 mM NaCl, adjusted to pH 7.5). The respective proportions of activated charcoal and Creon were 9:1, 15:1 and 25:1. Samples were centrifuged, the supernatant was filtered, and the amount of residual protein was quantified using a Bradford protein assay. A solution of 1 mg/ml Creon, and a 3 mg/ml suspension of activated charcoal were respectively used as positive and negative controls. As can be seen in FIG. 16, complete adsorption of the enzymes was obtained in 2 hours with a 15:1 ratio and in 1 hour with a 25:1 ratio.

The invention claimed is:

1. A formulation comprising:
   a) a substantially water-free core comprising a pellet of activated charcoal mixed with kappa-carrageenan, wherein the amount of kappa-carrageenan is between 5% and 25% by weight of the mixture of the activated charcoal with the kappa-carrageenan and wherein the amount of activated charcoal is between 75%-95% by weight of the mixture of the activated charcoal with the kappa-carrageenan, and
   b) a layer of an external coating formed around the core, wherein the external coating is a pH-dependent enterosoluble polymer selected from the group consisting of cellulose acetate trimellitate (CAT); cellulose acetate phthalate (CAP); anionic copolymers based on methylacrylate, methylmethacrylate and methacrylic acid; hydroxypropyl methylcellulose phthalate (HPMCP); hydroxypropylmethylcellulose acetate succinate (HPMCAS); methacrylic acid and ethyl acrylate copolymers; methacrylic acid and methyl methacrylate copolymers (in a 1:1 ratio); methacrylic acid and methyl methacrylate copolymers (in a 1:2 ratio); polyvinyl acetate phthalate (PVAP); and shellac resins, wherein the pH-dependent enterosoluble polymer dissolves at a pH equal to 6.0 and above.

2. The formulation of claim 1, wherein the amount of kappa-carrageenan is about 15% by weight of the mixture of the activated charcoal with the kappa-carrageenan.

3. The formulation of claim 1, wherein the pH-dependent enterosoluble polymer is selected from the group consisting of shellac; hydroxypropylmethylcellulose acetate succinate; hydroxypropylmethylcellulose phthalate; anionic copolymers based on methyl acrylate, methyl methacrylate and methacrylic acid; and methacrylic acid and methyl methacrylate copolymers (in a 1:2 ratio).

4. The formulation of claim 1, wherein the external coating is a mixture of (i) an anionic copolymer based on methyl acrylate, methyl methacrylate, and methacrylic acid, and (ii) a copolymer of methacrylic acid and ethyl acrylate, in a (i):(ii) weight ratio between 99:1 and 80:20.

5. The formulation of claim 1, wherein a further coating is provided between the core and the external pH-dependent layer, and wherein said further coating is selected from the group consisting of pH-dependent polymers, pH-independent water soluble polymers, pH-independent water insoluble polymers, and mixtures of a pH-dependent polymer and a water insoluble, pH-independent polymer.

6. The formulation of claim 5, wherein the pH-dependent polymer is selected from the group consisting of shellac polymers, anionic copolymers based on methylacrylate, methylmethacrylate and methacrylic acid, methacrylic acid and ethyl acrylate copolymer, hydroxypropyl methylcellulose phthalate (HPMCP), and hydroxypropylmethylcellulose acetate succinate (HPMCAS).

7. The formulation of claim 5, wherein the pH-independent water soluble polymer is selected from the group consisting of polyvinyl pyrrolidone (PVP) and high molecular weight cellulose polymers.

8. The formulation of claim 7, wherein the high molecular weight cellulose polymers are selected from the group consisting of hydroxypropylmethylcellulose (HPMC) and hydroxypropylcellulose (HPC).

9. The formulation of claim 5, wherein the pH-independent water insoluble polymers are selected from the group consisting of ethylcellulose polymers and copolymers of ethyl acrylate and methyl methacrylate.

10. The formulation of claim 5 wherein the mixtures of the pH-dependent polymer and the water insoluble, pH-independent polymer comprises a copolymer of ethylcellulose and ethyl acrylate methyl methacrylate.

11. The formulation according to claim 5, wherein the further coating comprises at least one cellulose derivative selected from the group consisting of hydroxypropylcellulose and ethylcellulose.

12. The formulation according to claim 5, wherein the further coating is made of a 1:9 to 9:1 weight ratio mixture of a methacrylic acid and ethyl acrylate copolymer and an ethyl acrylate and methyl methacrylate copolymer.

13. The formulation of claim 1, wherein the enterosoluble polymer layer is from 10% to 40% by weight of the total formulation.

14. The formulation of claim 1, wherein and the enterosoluble polymer layer is from 10% to 40% by weight of the total formulation.

15. The formulation of claim 1, wherein the pH-dependent enterosoluble polymer is an anionic copolymer based on methyl acrylate, methyl methacrylate and methacrylic acid.

16. The formulation of claim 1, wherein the activated charcoal is USP grade activated charcoal.

17. The formulation of claim 1, wherein the activated charcoal has a surface area above 1500 $m^2/g$.

18. A formulation comprising:
a) a core comprising activated charcoal mixed with kappa-carrageenan, wherein the amount of kappa-carrageenan is between 15% and 25% by weight of the mixture of the activated charcoal with the kappa-carrageenan and wherein the amount of activated charcoal is between 75%-85% by weight of the mixture of the activated charcoal with the kappa-carrageenan, and
b) a layer of an external coating formed around the core, wherein the external coating is a pH-dependent enterosoluble polymer selected from the group consisting of cellulose acetate trimellitate (CAT); cellulose acetate phthalate (CAP); anionic copolymers based on methylacrylate, methylmethacrylate and methacrylic acid; hydroxypropyl methylcellulose phthalate (HPMCP); hydroxypropylmethylcellulose acetate succinate (HPMCAS); methacrylic acid and ethyl acrylate copolymers; methacrylic acid and methyl methacrylate copolymers (in a 1:1 ratio); methacrylic acid and methyl methacrylate copolymers (in a 1:2 ratio); polyvinyl acetate phthalate (PVAP); and shellac resins, wherein the pH-dependent enterosoluble polymer dissolves at a pH equal to 6.0 and above.

19. A formulation comprising:
a) a core comprising a pellet of activated charcoal mixed with kappa-carrageenan, wherein the amount of kappa-carrageenan is between 5% and 25% by weight of the mixture of the activated charcoal with the kappa-carrageenan and wherein the amount of activated charcoal is between 75%-95% by weight of the mixture of the activated charcoal with the kappa-carrageenan, and
b) a layer of an external coating formed around the core, wherein the external coating is a pH-dependent enterosoluble polymer selected from the group consisting of cellulose acetate trimellitate (CAT); cellulose acetate phthalate (CAP); anionic copolymers based on methylacrylate, methylmethacrylate and methacrylic acid; hydroxypropyl methylcellulose phthalate (HPMCP); hydroxypropylmethylcellulose acetate succinate (HPMCAS); methacrylic acid and ethyl acrylate copolymers; methacrylic acid and methyl methacrylate copolymers (in a 1:1 ratio); methacrylic acid and methyl methacrylate copolymers (in a 1:2 ratio); polyvinyl acetate phthalate (PVAP); and shellac resins, wherein the pH-dependent enterosoluble polymer dissolves at a pH equal to 6.0 and above.

* * * * *